US009340587B2

(12) United States Patent
Thompson et al.

(10) Patent No.: US 9,340,587 B2
(45) Date of Patent: May 17, 2016

(54) ALBUMIN-FREE BOTULINUM TOXIN FORMULATIONS

(75) Inventors: Stewart A. Thompson, Burlingame, CA (US); Curtis L. Ruegg, Redwood City, CA (US); Jacob M. Waugh, San Francisco, CA (US)

(73) Assignee: Revance Therapeutics, Inc., Newark, CA (US)

( * ) Notice: Subject to any disclaimer, the term of this patent is extended or adjusted under 35 U.S.C. 154(b) by 243 days.

(21) Appl. No.: 12/824,118

(22) Filed: Jun. 25, 2010

(65) Prior Publication Data

US 2010/0330123 A1 Dec. 30, 2010

Related U.S. Application Data

(60) Provisional application No. 61/220,433, filed on Jun. 25, 2009.

(51) Int. Cl.

*A61K 39/08* (2006.01)
*C07K 14/33* (2006.01)
*A61K 8/49* (2006.01)
*A61K 8/60* (2006.01)
*A61K 8/64* (2006.01)
*A61Q 19/00* (2006.01)
*A61Q 19/08* (2006.01)

(52) U.S. Cl.

CPC ............... *C07K 14/33* (2013.01); *A61K 8/4973* (2013.01); *A61K 8/4993* (2013.01); *A61K 8/602* (2013.01); *A61K 8/64* (2013.01); *A61K 39/08* (2013.01); *A61Q 19/008* (2013.01); *A61Q 19/08* (2013.01)

(58) Field of Classification Search

None
See application file for complete search history.

(56) References Cited

U.S. PATENT DOCUMENTS 6,358,917 B1 * 3/2002 Carruthers et al. ........... 424/780
6,544,548 B1 4/2003 Siller-Jackson et al.
6,787,517 B1 * 9/2004 Gil et al. ........................... 514/1
6,844,324 B1 1/2005 Zhang et al.
7,807,780 B2 * 10/2010 Waugh et al. ................. 530/327
7,956,028 B2 * 6/2011 Garigapati et al. ............ 514/7.6
8,398,997 B2 * 3/2013 Dake et al. ................. 424/247.1
8,404,249 B2 * 3/2013 Dake et al. ................. 424/247.1
8,501,195 B2 * 8/2013 Turkel et al. ............... 424/239.1
8,518,414 B2 * 8/2013 Waugh ....................... 424/239.1
8,580,250 B2 * 11/2013 Hunt ........................... 424/94.3
8,895,506 B2 * 11/2014 Garigapati et al. ............ 514/7.6
8,920,795 B2 * 12/2014 Jung .................. A61K 38/4893 424/94.6
8,921,322 B2 * 12/2014 Favre et al. .................. 514/18.2
9,107,815 B2 * 8/2015 Hunt .................... A61K 9/0024
9,125,804 B2 * 9/2015 Webb .................. A61K 9/0019
9,180,081 B2 * 11/2015 Dake ....................... A61K 8/64
9,198,958 B2 * 12/2015 Jung .................. A61K 38/4893
2003/0147921 A1 8/2003 Goodnough et al.
2003/0229034 A1 * 12/2003 Waugh et al. .................. 514/44
2005/0214278 A1 9/2005 Kakuta et al.
2007/0196364 A1 8/2007 Krishnamurthy et al.
2008/0050352 A1 * 2/2008 Webb et al. ................ 424/93.41
2008/0069841 A1 * 3/2008 Panjwani et al. .......... 424/239.1
2008/0102090 A1 5/2008 Panjwani et al.
2008/0233152 A1 9/2008 Waugh et al.
2009/0010965 A1 1/2009 Eisele et al.
2009/0028906 A1 1/2009 Grein et al.
2011/0106021 A1 * 5/2011 Ruegg et al. .................. 604/290
2011/0237506 A1 * 9/2011 Garigapati et al. ............ 514/8.8
2012/0107361 A1 * 5/2012 Thompson et al. ........ 424/239.1
2012/0238969 A1 * 9/2012 Ruegg et al. .................. 604/290
2012/0294844 A1 * 11/2012 Waugh et al. ............. 424/94.67
2013/0224268 A1 * 8/2013 Alam et al. ................... 424/401
2014/0086900 A1 * 3/2014 Jung et al. .................. 424/94.67
2014/0099342 A1 * 4/2014 Edelson et al. ............... 424/400
2015/0064166 A1 * 3/2015 Jung ................. A61K 38/4893 424/94.67
2015/0320781 A1 * 11/2015 Dake ................ A61K 47/48192 424/174.1
2015/0322419 A1 * 11/2015 Ruegg ...................... C12N 9/52 435/220
2015/0328293 A1 * 11/2015 Webb .................. A61K 9/0019 424/94.67

FOREIGN PATENT DOCUMENTS

CN 1950100 A 9/2005
GB 2 416 122 1/2006
GB 2 419 526 5/2006
JP 2009-511485 3/2009
WO WO 2005/084410 A2 * 9/2005
WO WO 2009/015385 1/2009
WO WO 2010/090677 8/2010

OTHER PUBLICATIONS

International Search Report from corresponding PCT/US10/40104 dated Nov. 4, 2010.

Revance Therapeutics, Inc., English translation of the Notification for Reasons for Refusal issued in Japanese Patent Application No. 2012-517802, Jul. 10, 2014, 5 pages.

Akers, "Excipient-Drug Interactions in Parenteral Formulations," Journal of Pharmaceutical Sciences, vol. 91, No. 11, pp. 2283-2300, Nov. 2002.

Revance Therapeutics, Inc., Extended European Search Report issued in European Patent Application No. 10792770.9, Jul. 23, 2015, 7 pages.

* cited by examiner

*Primary Examiner* — Nita M Minnifield

(74) *Attorney, Agent, or Firm* — Kenneth H. Sonnenfeld; Leslie A. Serunian; King & Spalding LLP

(57) ABSTRACT

This invention relates to botulinum toxin formulations that are stabilized without the use of any proteinaceous excipients. The invention also relates to methods of preparing and using such botulinum toxin formulations.

146 Claims, 3 Drawing Sheets

FIGURE 3

SEQUENCE LISTING

<160> NUMBER OF SEQ ID NOS: 7

<210> SEQ ID NO 1

```
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Arg Lys Lys Arg Arg Gln Arg Arg Arg Gly Lys Lys Lys Lys Lys Lys
1               5                   10                  15

Lys Lys Lys Lys Lys Lys Lys Lys Lys Gly Arg Lys Lys Arg Arg Gln
            20                  25                  30

Arg Arg Arg
        35


<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Gly Arg Asp Asp Arg Arg Gln Arg Arg Arg Gly Lys Lys Lys Lys
1               5                   10                  15

Lys Lys Lys Lys Lys Lys Lys Lys Lys Lys Lys Gly Arg Gly Arg Asp
            20                  25                  30

Asp Arg Arg Gln Arg Arg Arg
        35


<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Tyr Gly Arg Lys Lys Arg Arg Gln Arg Arg Arg Gly Lys Lys Lys Lys
1               5                   10                  15

Lys Lys Lys Lys Lys Lys Lys Lys Lys Lys Lys Gly Tyr Gly Arg Lys
            20                  25                  30

Lys Arg Arg Gln Arg Arg Arg
        35


<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(20)
<223> OTHER INFORMATION: This region may encompass 0-20 "Gly" residues
<220> FEATURE:
<221> NAME/KEY: misc_feature
<222> LOCATION: (21)..(45)
<223> OTHER INFORMATION: This region may encompass 5, 7, 9, 11, 13, 15,
      17, 19, 21, 23, or 25 "Arg" residues
<220> FEATURE:
<223> OTHER INFORMATION: see specification as filed for detailed
      description of substitutions and preferred embodiments
```

<400> SEQUENCE: 4

```
Gly Gly Gly Gly Gly Gly Gly Gly Gly Gly Gly Gly Gly Gly Gly Gly
1               5                   10                  15

Gly Gly Gly Gly Arg Arg Arg Arg Arg Arg Arg Arg Arg Arg Arg Arg
            20                  25                  30

Arg Arg Arg Arg Arg Arg Arg Arg Arg Arg Arg Arg Arg
        35                  40                  45
```

<210> SEQ ID NO 5
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: misc_feature
<222> LOCATION: (1)..(20)
<223> OTHER INFORMATION: This region may encompass 0-20 “Gly” residues
<220> FEATURE:
<221> NAME/KEY: misc_feature
<222> LOCATION: (32)..(51)
<223> OTHER INFORMATION: This region may encompass 0-20 “Gly” residues
<220> FEATURE:
<223> OTHER INFORMATION: see specification as filed for detailed description of substitutions and preferred embodiments

<400> SEQUENCE: 5

```
Gly Gly Gly Gly Gly Gly Gly Gly Gly Gly Gly Gly Gly Gly Gly Gly
1               5                   10                  15

Gly Gly Gly Gly Arg Gly Arg Asp Asp Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50
```

<210> SEQ ID NO 6
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: misc_feature
<222> LOCATION: (1)..(20)
<223> OTHER INFORMATION: This region may encompass 0-20 “Gly” residues
<220> FEATURE:
<221> NAME/KEY: misc_feature
<222> LOCATION: (32)..(51)
<223> OTHER INFORMATION: This region may encompass 0-20 “Gly” residues
<220> FEATURE:
<223> OTHER INFORMATION: see specification as filed for detailed description of substitutions and preferred embodiments

<400> SEQUENCE: 6

```
Gly Gly Gly Gly Gly Gly Gly Gly Gly Gly Gly Gly Gly Gly Gly Gly
1               5                   10                  15

Gly Gly Gly Gly Tyr Gly Arg Lys Lys Arg Arg Gln Arg Arg Arg Gly
            20                  25                  30

Gly Gly Gly Gly Gly Gly Gly Gly Gly Gly Gly Gly Gly Gly Gly Gly
        35                  40                  45

Gly Gly Gly
    50
```

-continued

```
<210> SEQ ID NO 7
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(20)
<223> OTHER INFORMATION: This region may encompass 0-20 "Gly" residues
<220> FEATURE:
<221> NAME/KEY: misc_feature
<222> LOCATION: (30)..(49)
<223> OTHER INFORMATION: This region may encompass 0-20 "Gly" residues
<220> FEATURE:
<223> OTHER INFORMATION: see specification as filed for detailed
      description of substitutions and preferred embodiments

<400> SEQUENCE: 7

Gly Gly Gly Gly Gly Gly Gly Gly Gly Gly Gly Gly Gly Gly Gly Gly
1               5                   10                  15

Gly Gly Gly Gly Arg Lys Lys Arg Arg Gln Arg Arg Arg Gly Gly Gly
            20                  25                  30

Gly Gly Gly Gly Gly Gly Gly Gly Gly Gly Gly Gly Gly Gly Gly Gly
        35                  40                  45

Gly
```

ALBUMIN-FREE BOTULINUM TOXIN FORMULATIONS

This application claims priority to U.S. Provisional Patent Application No. 61/220,433, filed on Jun. 25, 2009, the contents of which are incorporated by reference in their entirety.

FIELD OF THE INVENTION

This invention relates to pharmaceutical formulations containing botulinum toxin. In particular, this invention relates to botulinum toxin formulations that are stabilized by non-proteinaceous excipients.

BACKGROUND OF THE INVENTION

Botulinum toxins (also known as botulin toxins or botulinum neurotoxins) are neurotoxins produced by *Clostridium botulinum* bacteria. Botulinum toxins produce paralysis of muscles by preventing synaptic transmission or release of acetylcholine across the neuromuscular junction. The action of botulinum toxins essentially blocks signals that normally would cause muscle spasms or contractions, resulting in paralysis.

There are eight naturally occurring serologically related botulinum toxins, seven of which are known to cause paralysis (viz., botulinum neurotoxin serotypes A, B, C, D, E, F and G). Each of these serotypes is distinguished by neutralization with type-specific antibodies. However, the molecular weight of the botulinum toxin protein molecule is about 150 kD for all seven of these active botulinum toxins. As released by the *Clostridium botulinum* bacteria, the botulinum toxin is present in a complex comprising the 150 kD botulinum toxin protein molecule along with associated non-toxin proteins. The total size of the complex may vary. For instance, the botulinum toxin type A complex can be produced by *Clostridium botulinum* bacteria as 900 kD, 500 kD and 300 kD complexes. Botulinum toxin types B and C complexes are only produced as 700 kD or 500 kD complexes. Botulinum toxin type D complexes are produced as both 300 kD and 500 kD complexes. Botulinum toxin types E and F complexes are only produced as 300 kD complexes. The complexes are believed to contain non-toxin hemaglutinin protein and non-toxin and non-toxic non-hemaglutinin protein. These two non-toxin proteins (which along with the botulinum toxin molecule comprise the relevant neurotoxin complex) are believed to provide stability against denaturation to the botulinum toxin molecule and protection against digestive acids when toxin is ingested.

While botulinum toxin is the most lethal naturally occurring toxin known to man, it has found extensive use as both a therapeutic and a cosmetic agent. For example, in 1986, the feasibility of using type A botulinum toxin for treatment of movement-associated wrinkles in the glabella area was first demonstrated by Schantz and Scott, in Lewis G E (Ed) *Biomedical Aspects of Botulinum*, N.Y.: Academic Press, 143-150 (1981). The use of botulinum type A for the treatment of wrinkles was published in 1992 (Schantz and Scott, in Lewis G. E. (Ed) *Biomedical Aspects of Botulinum*, N.Y.: Academic Press, 143-150 (1981)), and by 1994, other movement-associated wrinkles on the face were being treated with type A botulinum toxin (Scott, Opthalmol, 87:1044-1049 (1980)). The demand for cosmetic botulinum toxin treatments has grown steadily over the years, with current annual sales of botulinum toxin in the United States exceeding $ 1 billion dollars per year.

One challenging aspect of manufacturing commercial botulinum toxin formulations is stabilizing the botulinum toxin. Like many proteins, botulinum toxin may be degraded or denatured by environmental factors, such as heat, alkaline conditions, mechanical shear forces, or contact with reactive surfaces or substances. Furthermore, the difficulty in stabilizing the botulinum toxin in commercial formulations is exacerbated by the extreme toxicity of the toxin, which permits only minute amounts of toxin to be used for therapeutic purposes. If the botulinum toxin formulation is not properly stabilized, the minute amounts of botulinum toxin may undergo unwanted reactions and/or adhere to the inner surfaces of its storage containers, leading to unacceptable loss of botulinum toxin or activity.

Commercial botulinum toxin formulations are often distributed as lyophilized (i.e. freeze dried) or vacuum-dried powder, in order to prevent degradation and make the botulinum toxin formulation easier to handle and less expensive to transport. Prior to use, botulinum toxin powder formulations are reconstituted with a liquid carrier, such as water or a saline solution. For instance, one commercially available botulinum toxin formulation is sold under the trademark BOTOX® (Allergan, Inc., Irvine, Calif.). The BOTOX® formulation is distributed as a vacuum-dried powder stored in individual vials, each of which contains about 100 units (U) of *Clostridium botulinum* toxin type A complex, 0.5 milligrams of human serum albumin and 0.9 milligrams of sodium chloride. It has been reported that commercial botulinum toxin formulation must be stored at a temperature of −10° C. or less to maintain the labeled potency for the one year shelf life.

In commercial formulations of botulinum toxin, human serum albumin is often added as a bulk carrier and stabilizer. Generally, albumin may stabilize a therapeutic protein (e.g., botulinum toxin) by one or more of the following mechanisms: (1) reducing adhesion of the therapeutic protein to the inner surfaces of storage or dispensing containers, which include glassware, storage vials, and the syringe used to inject the pharmaceutical composition; and (2) reducing denaturation of the therapeutic protein, especially after reconstituting to prepare a solution of the therapeutic protein. Human serum albumin has the added advantage of being minimally immunogenic, which lessens the likelihood that a human patient will develop antibodies against the botulinum toxin formulation.

Although human serum albumin has been adopted as a stabilizer in commercial botulinum toxin formulations, there are still significant problems associated with this approach. One serious problem is that albumin is derived from blood and is therefore susceptible to carrying blood borne pathogens or infectious agents. For instance, the human serum albumin may carry the Human Immunodeficiency Virus (HIV). Albumin may also carry prions, which are proteinaceous infectious agents that are responsible for causing a neurodegenerative disorder known as Creutzfeldt-Jacob disease. The prions cause misfolding of proteins in the brain, resulting in dementia, memory loss, speech impairment, loss of motor coordination, and death, often within the span of months after the initial onset of symptoms.

Attempts to replace human serum albumin with non-proteinaceous stabilizers generally have been met with difficulties. A non-proteinaceous polymer may be reactive towards the botulinum toxin or may contain reactive impurities that degrade and/or denature the botulinum toxin. For example, some studies have used a poloxamer as a non-proteinaceous stabilizing compound for botulinum toxin. However, these studies report that reconstituted poloxamer-stabilized botulinum toxin formulations demonstrate low botulinum toxin activity, suggesting that the poloxamer excipient either failed to properly stabilize the botulinum toxin and/or induced unwanted degradation reactions to occur.

Accordingly, it would be highly desirable to have a botulinum toxin formulation that is stabilized, but without a proteinaceous excipient, especially without any animal-protein based excipients. Furthermore, it would be highly desirable to have a non-proteinaceous stabilizing excipient that does not itself react with botulinum toxin.

SUMMARY OF THE INVENTION

In one aspect, this invention relates to botulinum formulations that are stabilized by non-proteinaceous excipients. In particular, in preferred embodiments, this invention relates to botulinum toxin formulations that are stabilized without albumin or other animal protein-derived excipients.

One aspect of the invention is to provide a liquid composition comprising a botulinum toxin, a non-reducing disaccharide or a non-reducing trisaccharide, a non-ionic surfactant, and a physiologically compatible buffer capable of maintaining the pH between 4.5. and 6.5. The concentration of the non-reducing sugar in the liquid composition is in the range of 10% through 40% (w/v) and the concentration of the non-ionic surfactant is in the range of 0.005% through 0.5% (w/v).

Another aspect of the invention is to provide a powder composition by drying the liquid composition described above.

This invention also provides a method for stabilizing a botulinum toxin formulation. The method comprises combining a botulinum toxin, a non-reducing disaccharide or a non-reducing trisaccharide, a non-ionic surfactant, and physiologically compatible buffer components capable of maintaining the pH between 4.5 and 6.5 to form a liquid composition. The concentration of the non-reducing sugar in the liquid composition is in the range from 10% to 40% (w/v) and the concentration of the non-ionic surfactant is in the range from 0.005% to 0.5% (w/v). Optionally, the method further comprises drying the liquid composition to produce a stabilized powder composition.

Another aspect of the invention is to provide a liquid composition comprising a botulinum toxin, a non-reducing disaccharide or a non-reducing trisaccharide, a non-ionic surfactant, a bulking agent and a physiologically compatible buffer. In these embodiments, the concentration of the non-reducing disaccharide compositions is in the range of 0.50 to 3.0% (w/v), the concentration of the bulking agent is in the range of 1.5% to 7.5%, the concentration of the non-ionic surfactant is in the range of 0.005% to 0.5% (w/v); and the pH of the composition is in the range of 4.5 to 6.5. Also, the amount of non-reducing disaccharide or non-reducing trisaccharide relative to the amount of bulking agent is selected such that the bulking agent does not crystallize when the liquid composition is dried. The invention also expressly contemplates powder formulations prepared by drying such liquid compositions.

The invention also provides a method for stabilizing a botulinum toxin formulation comprising combining a botulinum toxin, a non-reducing disaccharide or a non-reducing trisaccharide, a non-ionic surfactant, a bulking agent and a physiologically compatible buffer to form a liquid composition. The concentration of the non-reducing disaccharide compositions is in the range of 0.50 to 3.0% (w/v), the concentration of the bulking agent is in the range of 1.5% to 7.5%, the concentration of the non-ionic surfactant is in the range of 0.005% to 0.5% (w/v); and the pH of the composition is in the range of 4.5 to 6.5. Optionally, the method further comprises drying the liquid composition to produce a stabilized powder composition. Also, the amount of non-reducing disaccharide or non-reducing trisaccharide relative to the amount of bulking agent is selected such that the bulking agent does not crystallize when the liquid composition is dried.

This invention also provides a liquid composition comprising a botulinum toxin, a non-reducing sugar, a non-ionic surfactant, a physiologically compatible buffer, a positively charged peptide and an optional bulking agent. The positively charged peptide has an amino acid sequence selected from the group consisting of RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), and YGRKKRRQRRR-G-$(K)_{15}$-G-YGRKKRRQRRR (SEQ ID NO: 3). The pH of the liquid composition is in the range of 4.5 to 6.5. The invention also expressly contemplates powder formulations prepared by drying such liquid compositions.

Yet another aspect of the invention is to provide a method for stabilizing a botulinum toxin formulation comprising combining a botulinum toxin, a non-reducing sugar, a non-ionic surfactant, a physiologically compatible buffer, a positively charged peptide and an optional bulking agent. The positively charged peptide has an amino acid sequence selected from the group consisting of RKKRRQRRR-G-$(K)_{15}$-G-RKKRRQRRR (SEQ ID NO: 1). RGRDDRRQRRR-G-$(K)_{15}$-G-RGRDDRRQRRR (SEQ ID NO: 2), and YGRKKRRQRRR-G-$(K)_{15}$-G-YGRKKRRQRRR (SEQ ID NO: 3). The pH of the liquid composition is in the range of 4.5 to 6.5. Optionally, the method further comprises drying the liquid composition to produce a stabilized powder composition.

BRIEF DESCRIPTION OF THE FIGURES

FIG. 3: Recovered botulinum toxin activity as a function of time after storage of a lyophilized botulinum toxin at different temperatures.

DETAILED DESCRIPTION OF THE INVENTION

Figure 1:
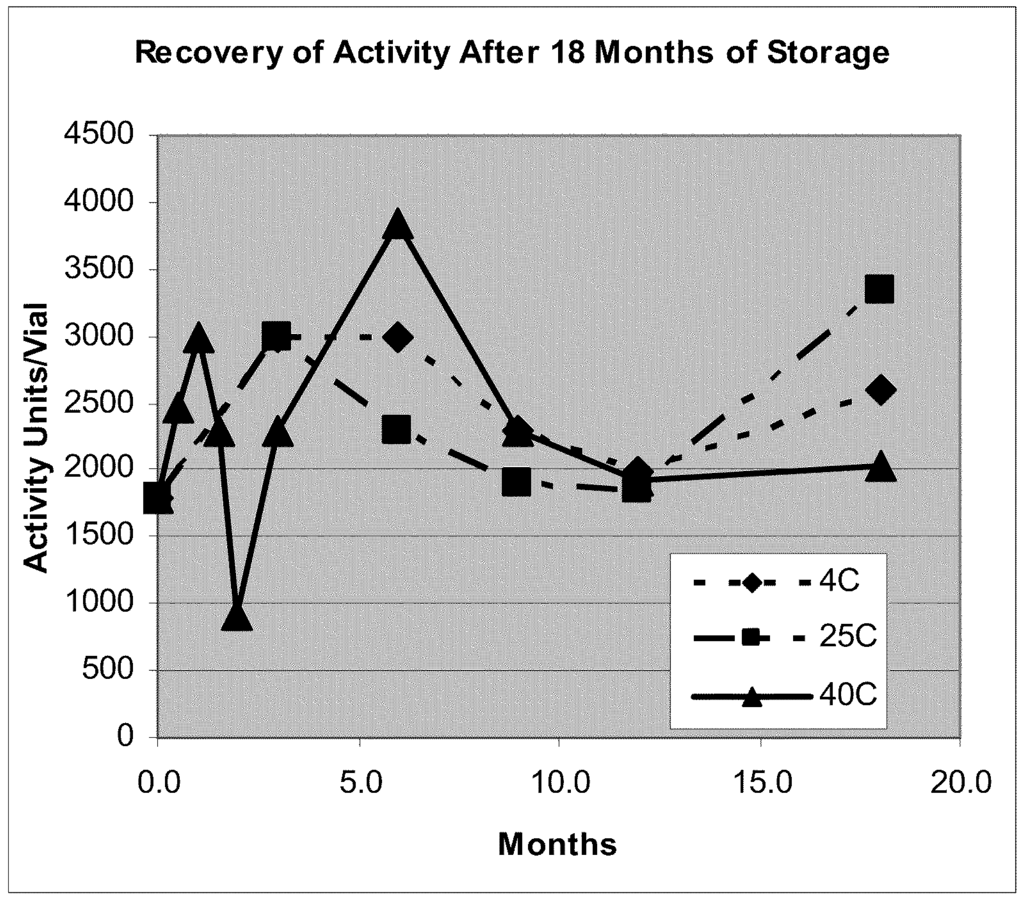
FIG. 1: Recovered botulinum toxin activity as a function of time after storage of a lyophilized botulinum toxin at 40° C.

This invention relates to botulinum toxin formulations that are stabilized without the addition of proteinaceous excipients derived (i.e., purified) from animal sources, such as albumin. As such, the botulinum formulations of the invention do not suffer from the potential problems associated blood borne pathogens or other types of infectious agents. This invention also provides methods for preparing botulinum toxin formulations without the addition of animal-derived proteinaceous excipients. In preferred embodiments, the formulations do not contain any proteinaceous excipients at all. However, in certain embodiments, proteinaceous excipients not derived from animal sources (e.g., recombinant albumin or recombinant gelatin) may be present in the formulations of the invention.

As used herein in connection with the botulinum toxin formulations of the invention, the term "stabilize" and variations thereof (e.g., "stabilization", "stabilizing" "stabilized" etc.) refers to the retention of biological activity of the botulinum toxin in the formulation over a specified time period as measured by a 20-mouse $LD_{50}$ assay (See L B Pearce, R E Borodic, *Tox. Appl. Pharmacol*, v 128, p 69, 1994 and ICCVAM/NICEATM/ECVAM, Scientific Workshop on Alternate Methods to Refine, Reduce and Replace the Mouse LD50 Assay for Botulinum Toxin Testing, 14 Nov. 2006). In preferred embodiments, there is 100% retention of the biological activity of the botulinum toxin over the specified time period. However, in other embodiments, there is at least a 10%, 20%, 30%, 40%, 50%, 60%, 70%, 80% or 90% retention of the biological activity of the botulinum toxin over the specified time period. In certain embodiments, the duration of the specified time period may be chosen to be consistent with the duration of the botulinum toxin product manufacturing processes. For instance, the duration of the specified time period may be chosen to be sufficient to stabilize the botulinum toxin as it is subjected to one or more processing steps. In other embodiments, the specified time will be on the order of weeks, months or even years, such as the case when the non-toxin formulation components are selected to permit long-term stabilization of the botulinum toxin formulation for storage. In certain embodiments, the specified time is at least two weeks, at least one month, at least three months, at least six months, at least nine months, at least one year, at least 18 months or at least two years. In other embodiments, the specified time is coincident with the time for botulinum toxin to retain a desired amount of bioactivity using the formulations of the invention, which time includes, for example, the duration of the activities stated above. The components used to stabilize the formulation may be selected to permit stabilization at low temperatures (e.g., −5 to −10° C.) or at ambient temperature, as described herein.

In some embodiments, the botulinum toxin formulations of the invention are provided in solid form. By way of example only, the formulations may be lyophilized or vacuum-dried to produce a solid formulation. When a botulinum toxin formulation of the invention is provided in solid form, and the specified time period over which stability of the botulinum formulation is measured is a week or less, the activity that is observed upon reconstitution is said to be the activity upon initial recovery. In certain preferred embodiments of the invention, there is at least a 70%, 80%, or 90% retention in the activity upon initial recovery. In other embodiments, there is at least a 90%, 91%, 92%, 93%, 94%, 95%, 96%, 97%, 98%, or 99% retention of activity upon initial recovery. In a particularly preferred embodiment, the activity upon initial recovery is greater than 99% and can even be 100%.

In other embodiments, the specified time over which stability is measured is greater than 12, 13, 14, 15, 16, 17, 18, 19, 20, 21, 22, 23, or 24 months at given storage temperature. When a botulinum toxin formulation of the invention is provided in solid form, and the specified time period over which stability of the botulinum formulation is measured twelve months or greater, the activity that is observed upon reconstitution is said to be the activity upon long term storage. In certain preferred embodiments, there is at least a 70%, 80%, or 90% retention of botulinum toxin activity upon long term storage. In certain embodiments there is a 90%, 91%, 92%, 93%, 94%, 95%, 96%, 97%, 98%, or 99° A retention of botulinum toxin activity upon long term storage. In certain embodiments, there is at least a 90% retention of botulinum toxin activity after 12, 13, 14, 15, 16, 17, 18, 19, 20, 21, 22, 23, or 24 months of storage at 25° C.; at least a 91% retention of botulinum toxin activity after 12, 13, 14, 15, 16, 17, 18, 19, 20, 21, 22, 23, or 24 months of storage at 25° C.; at least a 92% retention of botulinum toxin activity after 12, 13, 14, 15, 16, 17, 18, 19, 20, 21, 22, 23, or 24 months of storage at 25° C.; at least a 93% retention of botulinum toxin activity after 12, 13, 14, 15, 16, 17, 18, 19, 20, 21, 22, 23, or 24 months of storage at 25° C.; at least a 94% retention of botulinum toxin activity after 12, 13, 14, 15, 16, 17, 18, 19, 20, 21, 22, 23, or 24 months of storage at 25° C.; at least a 95% retention of botulinum toxin activity after 12, 13, 14, 15, 16, 17, 18, 19, 20, 21, 22, 23, or 24 months of storage at 25° C.; at least a 96% retention of botulinum toxin activity after 12, 13, 14, 15, 16, 17, 18, 19, 20, 21, 22, 23, or 24 months of storage at 25° C.; at least a 97% retention of botulinum toxin activity after 12, 13, 14, 15, 16, 17, 18, 19, 20, 21, 22, 23, or 24 months of storage at 25° C.; at least a 98% retention of botulinum toxin activity after 12, 13, 14, 15, 16, 17, 18, 19, 20, 21, 22, 23, or 24 months of storage at 25° C.; or at least a 99% retention of botulinum toxin activity after 12, 13, 14, 15, 16, 17, 18, 19, 20, 21, 22, 23, or 24 months of storage at 25° C.

In some embodiments of the invention, the botulinum toxin formulations are stored in liquid form, rather than solid form. In certain preferred embodiments, the liquid botulinum toxin formulations according to the invention retain at least 60%, 70%, 80%, or 90% of the botulinum toxin activity for up to 8 hours at room temperature. In a particularly preferred embodiment, liquid botulinum toxin formulations according to the invention retain 100% of the botulinum toxin activity for up to 8 hours at room temperature.

The excipients in the botulinum formulations of the invention advantageously reduce or eliminate mechanisms by which the botulinum toxin is lost during manufacturing and storage. Without wishing to be limited by theory, it is believed that the non-proteinaceous excipients of the invention reduce or eliminate unwanted adhesion of the botulinum toxin to the vessels used for manufacturing, storage, or delivery of the formulation. Non-limiting examples of such vessels includes those made with glass, polystyrene, polypropylene, and other polymers. Furthermore, and again without wishing to be limited by theory, it is believed that the non-proteinaceous excipients of the invention reduce or to prevent unwanted reactions between the botulinum toxin and objects or substances encountered by the botulinum toxin during manufacturing, storage, or delivery. In preferred embodiments, the non-proteinaceous excipients are inert to the other components of the formulation.

In some embodiments, the botulinum toxin formulations are prepared in a powder form for ease of handling, transport, or storage. The powder form may be prepared by any method known in the art. Non-limiting examples of such methods include lyophilization, vacuum-drying, drum-drying and spray drying, with lyophilization and vacuum-drying being particularly preferred.

The term "botulinum toxin" as used herein is meant to refer to any of the known types of botulinum toxin, whether produced by the bacterium or by recombinant techniques, as well as any such types that may be subsequently discovered including engineered variants or fusion proteins. As mentioned above, at the present time, seven immunologically distinct botulinum neurotoxins have been characterized, namely botulinum neurotoxin serotypes A, B, C, D, E, F and G, each of which is distinguished by neutralization with type-specific antibodies. The botulinum toxin serotypes are available from Sigma-Aldrich and from Metabiologics, Inc. (Madison, Wis.), as well as from other sources. The different serotypes of botulinum toxin vary in the animal species that they affect and in the severity and duration of the paralysis they evoke.

The botulinum toxin used in the compositions of this invention can alternatively be a botulinum toxin derivative, that is, a compound that has botulinum toxin activity but contains one or more chemical or functional alterations on any part or on any chain relative to naturally occurring or recombinant native botulinum toxins. For instance, the botulinum toxin may be a modified neurotoxin (e.g., a neurotoxin which has at least one of its amino acids deleted, modified or replaced, as compared to a native, or a recombinantly produced neurotoxin or a derivative or fragment thereof). For instance, the botulinum toxin may be one that has been modified in a way that, for instance, enhances its properties or decreases undesirable side effects, but that still retains the desired botulinum toxin activity. The botulinum toxin may be any of the botulinum toxin complexes produced by the bacterium, as described above. Alternatively, the botulinum toxin may be a toxin prepared using recombinant or synthetic chemical techniques (e.g. a recombinant peptide, a fusion protein, or a hybrid neurotoxin, as prepared from subunits or domains of different botulinum toxin serotypes (see U.S. Pat. No. 6,444,209, for instance)). The botulinum toxin may also be a portion of the overall molecule that has been shown to possess the necessary botulinum toxin activity, and in such case may be used per se or as part of a combination or conjugate molecule, for instance a fusion protein. Additionally, the botulinum toxin may be in the form of a botulinum toxin precursor, which may itself be non-toxic, for instance a nontoxic zinc protease that becomes toxic on proteolytic cleavage.

The term "botulinum toxin complex" or "toxin complex" as used herein refers to the approximately 150 kD botulinum toxin protein molecule (belonging to any one of botulinum toxin serotypes A-G), along with associated endogenous non-toxin proteins (i.e., hemagglutinin protein and non-toxin non-hemagglutinin protein produced by *Clostridium botulinum* bacteria). Note, however, that the botulinum toxin complex need not be derived from *Clostridium botulinum* bacteria as one unitary toxin complex. For example, botulinum toxin or modified botulinum toxin may be recombinantly prepared first and then subsequently combined with the non-toxin proteins. Recombinant botulinum toxin can also be purchased (e.g., from List Biological Laboratories, Campbell, Calif.) and then combined with non-toxin proteins.

This invention also contemplates "reduced botulinum toxin complexes," in which the botulinum toxin complexes have reduced amounts of non-toxin protein compared to the amounts naturally found in botulinum toxin complexes produced by *Clostridium botulinum* bacteria. In one embodiment, reduced botulinum toxin complexes are prepared using any conventional protein separation method to extract a fraction of the hemagglutinin protein or non-toxin non-hemagglutinin protein from botulinum toxin complexes derived from *Clostridium botulinum* bacteria. For example, reduced botulinum toxin complexes may be produced by dissociating botulinum toxin complexes through exposure to red blood cells at a pH of 7.3 (e.g., see EP 1514556 A1, hereby incorporated by reference). HPLC, dialysis, columns, centrifugation, and other methods for extracting proteins from proteins can be used. Alternatively, when the reduced botulinum toxin complexes are to be produced by combining synthetically produced botulinum toxin with non-toxin proteins, one may simply add less hemagglutinin or non-toxin non-hemagglutinin protein to the mixture than what would be present for naturally occurring botulinum toxin complexes. Any of the non-toxin proteins (e.g., hemagglutinin protein or non-toxin non-hemagglutinin protein or both) in the reduced botulinum toxin complexes according to the invention may be reduced independently by any amount. In certain exemplary embodiments, one or more non-toxin proteins are reduced by at least about 0.5%, 1%, 3%, 5%, 10%, 20%, 30%, 40%, 50%, 60%, 70%, 80%, or 90% compared to the amounts normally found in botulinum toxin complexes. In one embodiment, substantially all of the non-toxin protein (e.g., >95% of the hemagglutinin protein and non-toxin non-hemagglutinin protein) that would normally be found in botulinum toxin complexes derived from *Clostridium botulinum* bacteria is removed from the botulinum toxin complex. In another embodiment, only the pure botulinum toxin molecule, without any hemagglutinin protein and non-toxin non-hemagglutinin protein, is used. Furthermore, although the amount of endogenous non-toxin proteins may be reduced by the same amount in some cases, this invention also contemplates reducing each of the endogenous non-toxin proteins by different amounts, as well as reducing at least one of the endogenous non-toxin proteins, but not the others.

This invention also contemplates the general use of combinations and mixtures of botulinum toxins, although due to their differing nature and properties, mixtures of botulinum toxin serotypes are not generally administered at this time in the health-care or cosmetic industries.

The botulinum toxin formulations of the invention comprise a non-ionic surfactant. Generally, this invention contemplates the use of any non-ionic surfactant that has the ability to stabilize botulinum toxin and that is suitable for pharmaceutical use. In certain embodiments, the non-ionic surfactant is a polysorbate, non-limiting examples of which include polysorbate 20, polysorbate 40, polysorbate 60, and polysorbate 80. In other embodiments, the non-ionic surfactant is a sorbitan ester, non-limiting examples of which include sorbitan monolaurate, i.e., commercially known as SPAN® 20; sorbitan monostearate, i.e., commercially known as SPAN® 60 sorbitan tristearate, i.e., commercially known as Span SPAN® 65; and sorbitan monooleate, i.e., commercially known as SPAN® 80. The invention also contemplates the use of poloxamers, non-limiting examples of which include poloxamer 181, poloxamer 188, and poloxamer 407. The invention also contemplates using TRITON™ X-100, an octylphenol ethylene oxide, or NP-40, a nonylphenol ethoxylate, as the non-ionic surfactants. The foregoing types of non-ionic surfactants are commercially available, e.g., from Sigma-Aldrich Corp., St. Louis, Mo. In addition, the invention contemplates embodiments in which combinations of different non-ionic surfactants are used in conjunction. In certain preferred embodiments, the non-ionic surfactant is selected from the group consisting of polysorbates, poloxamers, and sorbitans, with polysorbates and sorbitans being particularly preferred. In preferred embodiments, the concentration of the non-ionic surfactant is in the range of 0.005% to 0.5%, or in the range of 0.01% to 0.2%, or in the range of 0.02% to 0.1% or in the range of 0.05 to 0.08%. This invention also contemplates formulations where the concentration of the non-ionic surfactant is 0.01%, 0.02%, 0.03%, 0.04%, 0.05%, 0.06%, 0.07%, 0.08%, 0.09%, 0.10%, 0.11%, 0.12%, 0.13%, 0.14%, or 0.15%.

The botulinum toxin formulations of the invention comprise a non-reducing sugar. In preferred embodiments, the non-reducing sugar has a glass transition temperature above 55° C., 57° C. or 60° C. Without wishing to be bound by theory, it is believed that such glass transition temperatures are sufficiently high to suppress undesirable molecular motions that cause the botulinum toxin to denature. In certain particularly preferred embodiments, the non-reducing sugar is a disaccharide, non-limiting examples of which include trehalose and sucrose. In other embodiments, the non-reducing sugar is a trisaccharide, a non-limiting example of which is raffinose. Generally, the concentration of the non-reducing sugar in the botulinum toxin formulations of the invention are in the range of 10% to 40% (w/v), preferably 10% to 25% (w/v), more preferably 15% to 20% (w/v). In some preferred embodiments, the concentration of the non-reducing sugar is 10%, 11%, 12%, 13%, 14%, 15%, 16%, 17%, 18%, 19% or 20% (w/v). When the non-reducing sugar is trehalose, preferably the hydrated form of trehalose (i.e., trehalose-dihydrate) is used to prepare the formulation, although use of the anhydrous form of trehalose is contemplated as well.

Furthermore, one aspect of this invention is the recognition that the choice of non-reducing sugar may be used to tailor the stability of the botulinum toxin formulation as a function of temperature. For instance, when the botulinum toxin formulation is subjected to conditions without refrigeration it is advantageous to use trehalose as the non-reducing sugar, because trehalose confers stability to the botulinum toxin at ambient temperatures. Thus, trehalose-containing formulations of the invention may be advantageously processed at ambient temperatures during various manufacturing processes without appreciable loss of botulinum toxin activity. In situations where the botulinum toxin formulation will be refrigerated (e.g., during long term storage lasting months or even years), one may choose sucrose as the non-reducing sugar. Mixtures of sugars are also contemplated by the invention. For example, in certain embodiments, both sucrose and trehalose are added to the botulinum toxin formulation. The specific ratio of components of the sugar mixture will depend upon the effect to be achieved and can be determined by routine experimentation. Also within the scope of this invention is the use of different non-reducing sugars, such as disaccharides, alone or in combination during different stages of purification, manufacturing, or storage. Thus, for example, trehalose may be used during initial processing and/or purification at higher temperatures (e.g., ambient temperature), followed by removal and replacement of the trehalose with sucrose. The removal and substitution of one non-reducing sugar, such as a disaccharide, for another may be accomplished by, for example, dialysis, chromatography, or other methods known in the art.

Another aspect of the invention is the recognition that the non-reducing sugar (or sugars) specified herein may, for certain embodiments, act as the primary bulking agent for solid botulinum toxin formulations. In particular, it has been discovered that the non-reducing sugars, when added in the amounts specified herein, can form a stable and mechanically robust cake upon lyophilization or vacuum-drying of the botulinum toxin formulation. Without wishing to be limited by theory, it is believed that the non-reducing sugars in such formulations form an amorphous solid in which the hydroxyl groups on the non-reducing sugar randomly orient the non-reducing sugar to maximize hydrogen bonding, which stabilizes the botulinum toxin and imparts mechanical robustness to the solid cake. In some preferred embodiments, the non-reducing sugars described herein are used as the sole bulking agent for the botulinum toxin formulations. In other preferred embodiments, a non-reducing sugar acts as the primary bulking agent, but small amounts of secondary bulking agents are added to the botulinum toxin formulation. The secondary bulking agents are not particularly limited, and may be any bulking agent that does not have an unacceptably adverse effect on the stability of the botulinum toxin formulation. When using secondary bulking agents that have a tendency to crystallize, it is preferable to add them in sufficiently low concentrations, so that they are unable to crystallize. Without wishing to be limited by theory, it is believed that crystallization of such secondary bulking agents would have an adverse effect on the stability of the solid cake obtained after lyophilization or vacuum-drying.

A further aspect of the invention is the unexpected result that non-reducing sugars, at the concentrations described herein, may be used not only to stabilize lyophilized botulinum toxin formulations, but also botulinum toxin formulations in the solution phase.

In preferred embodiments, the botulinum toxin formulation comprises a buffer. Generally, any physiologically compatible buffer capable of maintaining the pH in the range of 4.5 to 6.5, more preferably in the range of 5 to 6, and most preferably about 5.5, is suitable for the botulinum toxin formulations of the invention. Non-limiting examples of such buffers include those involving salts of citric acid, acetic acid, succinic acid, tartaric acid, maleic acid, and histidine. Non-limiting examples of suitable buffer concentrations include buffer concentrations in the range of 0.400% to 0.600%; 0.450% to 0.575%, or 0.500% to 0.565%. The invention also contemplates botulinum toxin formulations comprising a mixture of buffer salts, non-limiting examples of which include citrate/acetate, citrate/histidine, citrate/tartrate, maleate/histidine, or succinate/histidine. In certain preferred embodiments, the buffer is phosphate buffer.

In certain embodiments, the botulinum toxin formulations comprise a bulking agent (in addition to the non-reducing sugar(s)) which makes it easier to handle lyophilized forms of the botulinum toxin formulations. In certain preferred embodiments, the bulking agents crystallize under lyophilization conditions and do not mix well with the other excipients when in the solid state. However, in other preferred embodiments, the bulking agent remains amorphous under lyophilization conditions, even if it is known to have a tendency to crystallize during freezing (e.g., mannitol or glycine). As will be understood by a person of ordinary skill in the art, whether a bulking agent will crystallize or remain amorphous during lyophilization is governed by several factors, including the type of bulking agent, the amount of bulking agent relative to the other components of the formulation, and the rate at which the formulation is lyophilized. In certain preferred embodiments, the amount of non-reducing sugar relative to bulking agent is adjusted to suppress the crystallization of the bulking agent. When this is the case, the ratio of non-reducing sugar to bulking agent, on a weight percent basis, may be greater than 0.33 to 1; 0.5 to 1, 0.75 to 1; 1:1; 2:1, 3:1, or 4:1. Non-limiting examples of bulking agents contemplated by the invention include sorbitol, mannitol, glycine, arginine, and histidine. In some embodiments, the concentration of the bulking agent may be in the range of 1% to 10%, 2% to 6%, 3% to 5% or 4% to 4.5% (w/v). In certain preferred embodiments, when a bulking agent is used, the concentration of the non-reducing sugar may be reduced from the 10% to 40% (w/v) range to a range of 0.5% to 3.0% (w/v). Furthermore, in certain preferred embodiments, the ratio of the non-reducing sugar to the bulking agent is in the range of 0.07 to 2.0, preferably in the range of 0.4 to 0.6. Thus, by way of example only, the formulation may comprise mannitol as the bulking agent and trehalose dihydrate as the non-reducing sugar, with mannitol present in a concentration range of 1.5% to 7.5% (w/v) and trehalose dihydrate present in a concentration range of 0.5% to 3.0% (w/v). Preferably, the bulking agent is not sodium chloride.

The botulinum toxin formulations of the invention can be administered via any conventional route of administration. In some embodiments of the invention, the botulinum toxin formulations are administered by intramuscular or subcutaneous injection into to the subject. In other embodiments, the botulinum toxin formulations are administered topically. Regardless of whether the botulinum toxin formulations are administered topically or by injection, the formulations may include a positively charged carrier having positively charged efficiency groups, as described herein, in order to facilitate the penetration of the botulinum toxin into the issues of interest. It should be noted, however, that the positively charged carrier is not required for stabilization and that the invention contemplates embodiments in which the formulations do not comprise such a positively charged carrier. The botulinum toxin formulations of the invention may also be administered via a drug delivery device, a non-limiting example of which is a skin patch.

When the botulinum toxin formulations are to be administered topically, it is advantageous to include in the formulations a positively charged carrier with positively charged branching groups, as described herein, to promote transdermal penetration of the botulinum toxin (see also U.S. patent application Ser. Nos. 09/910,432; 11/073,307; 11/072,026; and 10/793,138, each of which is incorporated by reference in its entirety). Without the use of the positively charged carrier or some other means of enhancing transdermal transport, the transdermal flux of topically applied botulinum toxin would be expected to be quite low. It should be noted that the invention also contemplates the use of other methods of enhancing transdermal transport, besides the use of a positively charge carrier as described herein, with the botulinum toxin formulations of the invention. Non-limiting examples of such methods include transdermal delivery of the botulinum toxin formulations using liposomes, iontophoresis, micelles, and the like.

Furthermore, when the botulinum toxin formulations are to be administered topically, it is often advantageous to mix them with gelling agents and/or viscosity-modifying agents to increase the viscosity of the formulation, order make the application of the botulinum toxin easier and more accurate. Additionally, if a positively charged carrier is used, these agents help to prevent the aqueous botulinum toxin/carrier formulation from drying out, which tends to cause a decrease in the activity of the botulinum toxin. Particularly preferred agents are those that are uncharged and do not interfere with the botulinum toxin activity or the efficiency of the toxin-carrier complexes in crossing skin. The gelling agents may be certain cellulose-based gelling agents, such as hydroxypropylcellulose (HPC) for example. In some embodiments, the botulinum toxin/carrier complex is formulated in a composition having 2-4% HPC. Alternatively, the viscosity of a solution containing a botulinum toxin/carrier complex may be altered by adding polyethylene glycol (PEG). In other embodiments, the botulinum toxin/carrier solution is combined with pre-mixed viscous agents, such as Cetaphil® moisturizer. In other embodiments, the viscosity modifying agent is a poloxamer, non-limiting examples of which include poloxamer 188 and poloxamer 407. The viscosity-modifying agent may also be a polyacrylic acid, a polyamide, or a vegetable gum (e.g., guar gum). Furthermore, botulinum toxin formulations as described herein may be mixed with excipients to form emulsions (including microemulsions), suspensions, creams, lotions, gels, powders, or other typical solid or liquid compositions used for application to skin and other tissues where the compositions may be used. Such compositions may also contain other ingredients typically used in such products, such as antimicrobials, moisturizers and hydration agents, penetration agents, preservatives, emulsifiers, natural or synthetic oils, solvents, surfactants, detergents, emollients, antioxidants, fragrances, fillers, thickeners, waxes, odor absorbers, dyestuffs, coloring agents, powders, and optionally anesthetics, anti-itch additives, botanical extracts, conditioning agents, darkening or lightening agents, glitter, humectants, mica, minerals, polyphenols, silicones or derivatives thereof, sunblocks, vitamins, and phytomedicinals.

This invention also provides kits for preparing and/or administering the botulinum toxin formulations of the invention. In some embodiments, the kit comprises the botulinum toxin, as well as such additional excipients that are needed to produce a stabilized formulation according to the invention. The kit may also comprise a premix that may in turn be used to produce such a formulation. In other embodiments, the kit comprises a botulinum toxin formulation according to the invention that has been lyophilized and a device for delivering the formulation, a non-limiting example of which is a syringe.

The invention provides formulations that deliver a "therapeutic amount" of botulinum to the subject during treatment. As used herein, the term "therapeutic amount" refers to an amount of botulinum toxin that is sufficient to produce the desired effect (e.g., relaxation of muscles, treatment of wrinkles, treatment of pain, or reduction of activity of an overactive gland, such as a sweat gland). The "therapeutic amount" of botulinum toxin is implicitly understood to be a safe amount that does not cause unwanted paralysis or other undesired or harmful side effects. The specific amount of botulinum toxin that is administered will depend on several factors, including the route of administration, the site of administration, the indication to be treated, and the serotype (or serotypes) of botulinum toxin in the specific formulation. For instance, when the type A serotype botulinum toxin is selected, a therapeutic amount may be in the range of 10 U to 150 U or 1,000 U to 2,500 U. In other preferred embodiments, the therapeutic amount ranges from 400 U to 800 U and 1,000 U to 50,000 U, preferably from 2,000-35,000 U, more preferably from 3,000 U-30,000 U, and even more preferably from 4,000 U to 25,000 U. In certain embodiments, the therapeutic amount ranges from 4,000 U to 8,000 U, 9,000 U to 19,000 U, or 20,000 U to 40,000 U.

The compositions of the invention are applied so as to cause a desired effect, which may be a cosmetic or a therapeutic effect. Desired effects include the relaxation of certain muscles with the aim of, for instance, decreasing the appearance of fine lines and/or wrinkles, especially in the face, or adjusting facial appearance in other ways such as widening the eyes, lifting the corners of the mouth, or smoothing lines that fan out from the upper lip, or the general relief of muscular tension. The last-mentioned effect, general relief of muscular tension, can be effected in the face or elsewhere. The compositions of the invention may contain an appropriate effective amount of the botulinum toxin for application as a single-dose treatment, or may be more concentrated, either for dilution at the place of administration or for use in multiple applications. The stabilized botulinum toxin complexes or stabilized reduced botulinum toxin complexes can be administered to a subject for treating conditions such as undesirable facial muscle or other muscular spasms, hyperhidrosis, acne, or conditions elsewhere in the body in which relief of muscular ache or spasms is desired. The botulinum toxin is administered delivery to muscles or to other skin-associated structures. The administration may be made, for example, to the face, legs, shoulders, back (including lower back), axilla, palms, feet, neck, groin, dorsa of the hands or feet, elbows, upper arms, knees, upper legs, buttocks, torso, pelvis, or any other part of the body where administration of the botulinum toxin is desired.

In certain preferred embodiments, the botulinum toxin formulations of the invention comprise a positively charged carrier with positively charged efficiency groups. When this is the case, the positively charged carrier is present in an amount sufficient to facilitate penetration of the botulinum toxin into the tissues of interest. As used herein, the term "positively charged" means that the carrier has a positive charge under at least some solution-phase conditions, more preferably under at least some physiologically compatible conditions. More specifically, "positively charged" means that the group in question contains functionalities that are charged under all pH conditions, for instance, a quaternary amine, or contains a functionality which can acquire positive charge under certain solution-phase conditions, such as pH changes in the case of primary amines. More preferably, "positively charged" as used herein refers to those groups that have the behavior of associating with anions over physiologically compatible conditions. Polymers with a multiplicity of positively-charged moieties need not be homopolymers, as will be apparent to one skilled in the art. Other examples of positively charged moieties are well known in the prior art and can be employed readily, as will be apparent to those skilled in the art.

Generally, the positively-charged carrier comprises a positively charged backbone, which is typically a chain of atoms, either with groups in the chain carrying a positive charge at physiological pH, or with groups carrying a positive charge attached to side chains extending from the backbone. Preferably, the positively charged backbone itself will not have a defined enzymatic or therapeutic biologic activity. The linear backbone is a hydrocarbon backbone which is, in some embodiments, interrupted by heteroatoms selected from nitrogen, oxygen, sulfur, silicon and phosphorus. The majority of backbone chain atoms are usually carbon. Additionally, the backbone will often be a polymer of repeating units (e.g., amino acids, poly(ethyleneoxy), poly(propyleneamine), polyalkyleneimine, and the like) but can be a heteropolymer. In one group of embodiments, the positively charged backbone is a polypropyleneamine wherein a number of the amine nitrogen atoms are present as ammonium groups (tetra-substituted) carrying a positive charge. In another embodiment, the positively charged backbone is a nonpeptidyl polymer, which may be a hetero- or homo-polymer such as a polyalkyleneimine, for example a polyethyleneimine or polypropyleneimine, having a molecular weight of from about 100 to about 2,500,000 D, preferably from about 250 to about 1,800,000 D, and most preferably from about 1000 to about 1,400,000 D. In another group of embodiments, the backbone has attached a plurality of side-chain moieties that include positively charged groups (e.g., ammonium groups, pyridinium groups, phosphonium groups, sulfonium groups, guanidinium groups, or amidinium groups). The sidechain moieties in this group of embodiments can be placed at spacings along the backbone that are consistent in separations or variable. Additionally, the length of the sidechains can be similar or dissimilar. For example, in one group of embodiments, the sidechains can be linear or branched hydrocarbon chains having from one to twenty carbon atoms and terminating at the distal end (away from the backbone) in one of the above-noted positively charged groups. In all aspects of the present invention, the association between the carrier and the botulinum toxin is by non-covalent interaction, non-limiting examples of which include ionic interactions, hydrogen bonding, van der Waals forces, or combinations thereof.

In one group of embodiments, the positively charged backbone is a polypeptide having multiple positively charged sidechain groups (e.g., lysine, arginine, ornithine, homoarginine, and the like). Preferably, the polypeptide has a molecular weight of from about 100 to about 1,500,000 D, more preferably from about 250 to about 1,200,000 D, most preferably from about 1000 to about 1,000,000 D. One of skill in the art will appreciate that when amino acids are used in this portion of the invention, the sidechains can have either the D- or L-form (R or S configuration) at the center of attachment. In certain preferred embodiments, the polypeptide has a molecular weight from about 500 to about 5000 D, more preferably from 1000 to about 4000 D, more preferably from 2000 to about 3000 D. In other embodiments, the polypeptide has a molecular weight of at least about 10,000.

In another embodiment, the backbone portion is a polylysine and efficiency groups, as discussed herein, are attached to the polylysine. The polylysine may have a molecular weight of from about 100 to about 1,500,000 D, preferably from about 250 to about 1,200,000 D, and most preferably from about 1000 to about 3000 D. In one exemplary embodiment, the positively charged carrier with positively charged efficiency groups is a peptide with the amino acid sequence RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), or YGRKKRRQRRR-G-$(K)_{15}$-G-YGRKKRRQRRR (SEQ ID NO: 3). It also can be any of the commercially available (Sigma Chemical Company, St. Louis, Mo., USA) polylysines such as, for example, polylysine having MW>70,000 D, polylysine having MW of 70,000 to 150,000 D, polylysine having MW 150,000 to 300,000 D and polylysine having MW>300,000 D. The selection of an appropriate polylysine will depend on the remaining components of the composition and will be sufficient to provide an overall net positive charge to the composition and provide a length that is preferably from one to four times the combined length of the negatively charged components.

Alternatively, the backbone can be an analog of a polypeptide such as a peptoid. See, for example, Kessler, *Angew. Chem. Int. Ed. Engl.* 32:543 (1993); Zuckermann et al. *Chemtracts—Macromol. Chem.* 4:80 (1992); and Simon et al. *Proc. Nat'l. Acad. Sci*. USA 89:9367 (1992)). Briefly, a peptoid is a polyglycine in which the sidechain is attached to the backbone nitrogen atoms rather than the alpha-carbon atoms. As above, a portion of the sidechains will typically terminate in a positively charged group to provide a positively charged backbone component. Synthesis of peptoids is described in, for example, U.S. Pat. No. 5,877,278, which is hereby incorporated by reference in its entirety. As the term is used herein, positively charged backbones that have a peptoid backbone construction are considered "non-peptide" as they are not composed of amino acids having naturally occurring sidechains at the α-carbon locations.

A variety of other backbones can be used employing, for example, steric or electronic mimics of polypeptides wherein the amide linkages of the peptide are replaced with surrogates such as ester linkages, thioamides (—CSNH—), reversed thioamide (—NHCS—), aminomethylene (—$NHCH_2$—) or the reversed methyleneamino (—$CH_2NH$—) groups, keto-methylene (—$COCH_2$—) groups, phosphinate (—$PO_2RCH_2$—), phosphonamidate and phosphonamidate ester (—$PO_2RNH$—), reverse peptide (—NHCO—), trans-alkene (—CR═CH—), fluoroalkene (—CF═CH—), dimethylene (—$CH_2CH_2$—), thioether (—$CH_2S$—), hydroxyethylene (—$CH(OH)CH_2$—), methyleneoxy (—$CH_2O$—), tetrazole ($CN_4$), sulfonamido (—$SO_2NH$—), methylenesulfonamido (—$CHRSO_2NH$—), reversed sulfonamide (—$NHSO_2$—), and backbones with malonate and/or gem-diamino-alkyl subunits, for example, as reviewed by Fletcher et al. ((1998) Chem. Rev. 98:763) and detailed by references cited therein. Many of the foregoing substitutions result in approximately isosteric polymer backbones relative to backbones formed from α-amino acids.

In each of the backbones provided above, sidechain groups can be appended that carry a positively charged group. For example, the sulfonamide-linked backbones (—$SO_2NH$— and —$NHSO_2$—) can have sidechain groups attached to the nitrogen atoms. Similarly, the hydroxyethylene (—CH(OH)

$CH_2$—) linkage can bear a sidechain group attached to the hydroxy substituent. One of skill in the art can readily adapt the other linkage chemistries to provide positively charged sidechain groups using standard synthetic methods.

In some embodiments of the invention, the positively charged carrier comprises positively charged efficiency groups. Non-limiting examples of efficiency groups include -$(gly)_{n1}$-$(arg)_{n2}$ (SEQ ID NO: 4), in which the subscript n1 is an integer of from 0 to 20 more preferably 0 to 8, still more preferably 2 to 5, and the subscript n2 is independently an odd integer of from about 5 to about 25, more preferably from about 7 to about 17, and most preferably from about 7 to about 13, HIV-TAT or fragments thereof, or Antennapedia PTD or a fragment thereof. Preferably the side-chain or branching groups have the general formula -$(gly)_{n1}$-$(arg)_{n2}$ (SEQ ID NO: 4) as described above. Other preferred embodiments are those in which the branching or efficiency groups are HIV-TAT fragments that have the formula $(gly)_p$-RGRDDRRQRRR-$(gly)_q$ (SEQ ID NO: 5), $(gly)_p$-YGRKKRRQRRR-$(gly)_q$ (SEQ ID NO: 6), or $(gly)_p$-RKKRRQRRR-$(gly)_q$ (SEQ ID NO: 7), wherein the subscripts p and q are each independently an integer of from 0 to 20 and the fragment is attached to the carrier molecule via either the C-terminus or the N-terminus of the fragment. The side branching groups can have either the D- or L-form (R or S configuration) at the center of attachment. Preferred HIV-TAT fragments are those in which the subscripts p and q are each independently integers of from 0 to 8, more preferably 2 to 5. Other preferred embodiments are those in which the branching groups are Antennapedia PTD groups or fragments thereof that retain the group's activity. These are known in the art, for instance, from Console et al., *J. Biol. Chem.* 278: 35109 (2003). Preferably, the positively charged carrier includes side-chain positively charged branching groups in an amount of at least about 0.05%, as a percentage of the total carrier weight, preferably from about 0.05 to about 45 weight %, and most preferably from about 0.1 to about 30 weight %. For positively charged branching groups having the formula -$(gly)_{n1}$-$(arg)_{n2}$ (SEQ ID NO: 4), the most preferred amount is from about 0.1 to about 25%.

The following examples are meant to provide non-limiting illustrations of various embodiments of the invention. As a person of ordinary skill in the art will recognize, modifications may be made without departing from the spirit and the scope of the invention.

EXAMPLES

Example 1

Preparation of a Botulinum Toxin Formulation

An exemplary botulinum toxin formulation of the invention was prepared by combining appropriate amounts of trehalose dihydrate, polysorbate-20, histidine, and histidine HCl to produce a 2× formulation stock solution that contained 36% trehalose dihydrate, 0.05% polysorbate-20, and 1.126% histidine at a pH of 5.5. The solution was cooled to 4° *C. Botulinum* toxin API was pelleted by centrifugation from an ammonium sulfate stock suspension. The toxin pellet was dissolved in 0.56% histidine buffer pH 5.5 with 0.05% polysorbate-20. This solution was further diluted with the histidine/polysorbate-20 solution to give a toxin stock solution of 1.074 μg/mL solution.

A stock solution of the carrier peptide RKKRRQRRR-G-$(K)_{15}$-G-RKKRRQRRR (SEQ ID NO: 1) was prepared by dissolving sufficient peptide into water to produce a solution of 6.0 mg/ml, peptide. Toxin stock solution, peptide stock solution, 0.56% histidine buffer, and 2× formulation stock solution were combined to produce a formulation bulk drug product consisting of 18% trehalose dihydrate, 0.025% polysorbate-20, 0.56% histidine buffer, 55 ng/mL toxin and 150 μg/mL carrier peptide.

Example 2

Lyophilization of a Botulinum Toxin Formulation

This example provides a lyophilization procedure for a botulinum toxin formulation according to the invention. 200 μL aliquots of the formulation bulk drug product described in Example 1 was transferred to each of fifty-five 2-mL glass vials. Grey butyl rubber lyophilization stoppers were loosely placed on top of the glass vials. The vials were placed into the lyophilizer and lyophilization initiated.

The lyophilization process comprised three main stages: (1) a freezing stage; (2) a primary drying stage; and (3) a secondary drying stage. Each of these three main stages contained one or more individual process steps, which were performed at the temperatures and pressures as indicated below. The primary drying time required to complete primary drying varied depending upon the number of vials and the fill volume in the vials.

Freezing

| Step | Rate/Hold | deg C. | Minutes |
|---|---|---|---|
| 1 | H | 5 | 50 |
| 2 | R | −45 | 60 |
| 3 | H | −45 | 120 |

Freeze, Condenser and Evacuate:

| | |
|---|---|
| Freeze Temperature: | −40 deg C. Shelf or Product Ave |
| Extra Freeze Time: | 0 minutes |
| Vacuum Start Permit: | −45 Avg Cond deg C. |
| Heat Start Permit: | 200 mTorr |

Primary Drying

| Step | Rate/Hold | deg C. | Minutes | mTorr |
|---|---|---|---|---|
| 1 | H | −45 | 150 | 150 |
| 2 | H | −33 | 2520 | 150 |
| 3 | R | −25 | 990 | 150 |
| 4 | H | −25 | 275 | 150 |
| 5 | H | −15 | 240 | 150 |
| 6 | H | 0 | 300 | 150 |
| 7 | R | 25 | 180 | 150 |
| 8 | H | 25 | 120 | 150 |

Secondary Drying

| Step | | | | |
|---|---|---|---|---|
| 1 | H | 27 | 160 | 100 |

Example 3

Stability of Botulinum Toxin Formulation with Trehalose Dihydrate

Figure 2:
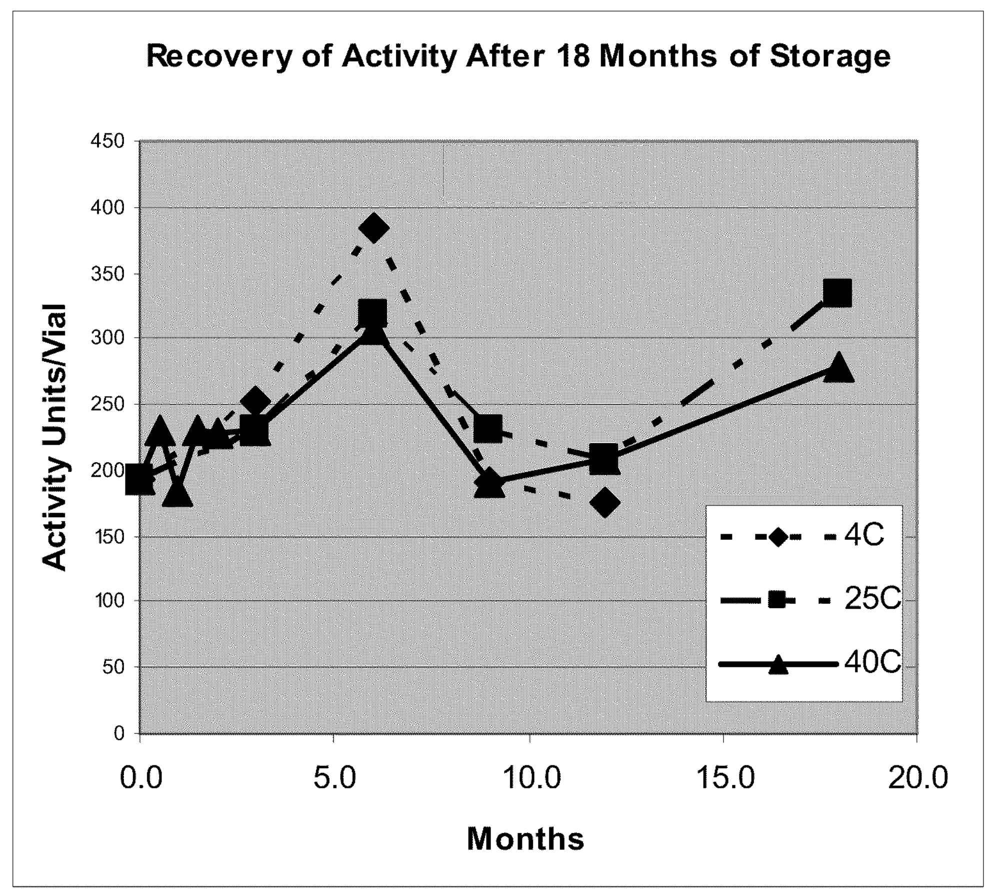
FIG. 2: Recovered botulinum toxin activity as a function of time after storage of a lyophilized botulinum toxin at different temperatures.

FIGS. 1 and 2 show the results of stability studies in which vials of the botulinum toxin formulation prepared at two different toxin concentrations with trehalose dihydrate (11 ng/vial and 1.1 ng/vial) were prepared as described above, stored at 4° C., 25° C. and 40° C. and tested at the indicated time points to determine the biological activity of the botulinum toxin for a duration of up to 18 months. The activity was measured using the $LD_{50}$ mouse assay and the activities are reported in FIGS. 1 and 2 as equivalent units of botulinum toxin per vial. At the beginning of the experiment (t=0), the observed activity was 1802 units of botulinum toxin per vial for the formulation in FIG. 1 and 192 units of botulinum toxin per vial for the formulation in FIG. 2. The observed variability in the botulinum toxin activity in FIGS. 1 and 2 is believed to result from the inherent noise in the data obtained using the $LD_{50}$ mouse assay and the small sample number (n=1 vial/temperature-timepoint). Despite this variability, the data indicate that there is no trend to loss of recovered activity over this eighteen-month study, even at a storage temperature of 40° C. These data provide an example of the stabilization of an exemplary botulinum toxin formulation of the invention.

Example 4

Stability of Botulinum Toxin Formulation with Sucrose

Figure 3:
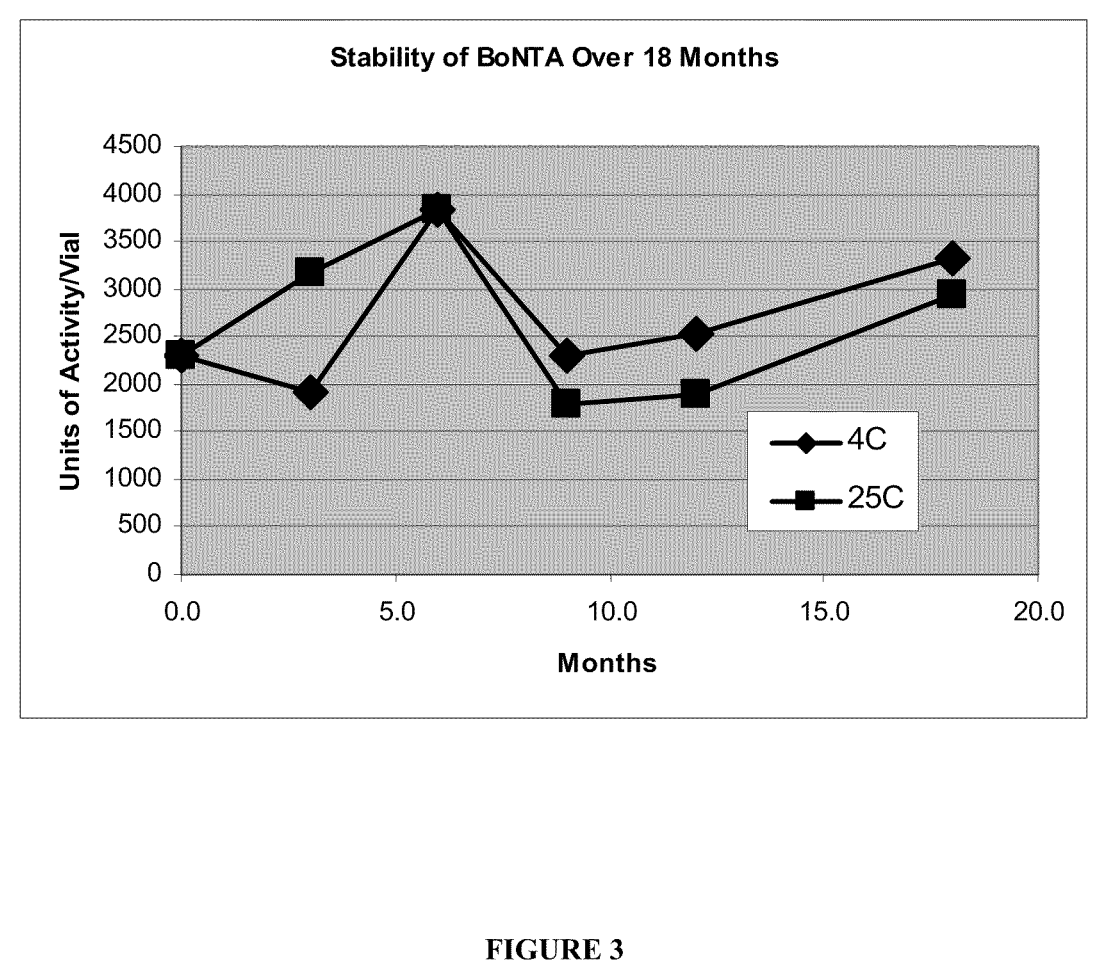

FIG. 3 shows the results of stability studies in which vials of the botulinum toxin formulation with sucrose at 11 ng/vial were prepared using the protocol described above for the trehalose-containing formulations, stored at 4° C. and 25° C. and tested at the indicated time points to determine the biological activity of the botulinum toxin for a duration of up to 18 months. The activity was measured using the $LD_{50}$ mouse assay as described above and the activities are reported in FIG. 3 as equivalent units of botulinum toxin per vial. At the beginning of the experiment (t=0), the observed activity was 2299 units of botulinum toxin per vial. The observed variability in the botulinum toxin activity in FIG. 3 is believed to result from the inherent noise in the data obtained using the $LD_{50}$ mouse assay and the small sample number (n=1 vial/temperature-timepoint). Despite this variability, the data indicate that there is no trend to loss of recovered activity over this eighteen-month study, even at a storage temperature of 25° C. These data provide an example of the stabilization of an exemplary botulinum toxin formulation of the invention.

Example 5

Lyophilization of a Botulinum Toxin Formulation with Bulking Agents

In this example, the botulinum toxin formulation was prepared by combining appropriate amounts of trehalose dihydrate, mannitol, polysorbate-20, histidine, and histidine HCl to produce a formulation stock solution that contained 3% trehalose dihydrate, 7.5% mannitol, 0.05% polysorbate-20, and 0.563% histidine at a pH of 5.5. The solution was cooled to 4° C. Botulinum toxin API was pelleted by centrifugation from an ammonium sulfate stock suspension. The toxin pellet was dissolved in the formulation stock solution. The concentration of this solution was 117 μg/mL. This solution was further diluted with the same solution to a final toxin stock solution concentration of 11.7 μg/mL. A sufficient amount of a carrier peptide having the amino acid sequence RKKRRQRRR-G-$(K)_{15}$-G-RKKRRQRRR (SEQ ID NO: 1) was dissolved in water to prepare a 20 mg/mL carrier peptide stock solution. These solutions were combined to create a formulation bulk drug product with a final composition of 3% trehalose dihydrate, 7.5% mannitol, 0.05% polysorbate-20, and 0.563% histidine pH of 5.5, 75 μg/mL carrier peptide, and 5.5 ng/mL toxin, Aliquots of 200 μL of the formulation bulk drug product were added to each of 192 2-mL glass lyophilization vials. Grey Butyl rubber stoppers were placed loosely on top of the vials. The vials were then placed in the lyophilizer and lyophilization was initiated.

As in the previous example, the lyophilization process comprised three main stages: (1) a freezing stage; (2) a primary drying stage; and (3) a secondary drying stage. Each of these three main stages contained one or more individual process steps, which were performed at the temperatures and pressures as indicated below:

Freezing

| Step | Rate/Hold | deg C. | Minutes |
|---|---|---|---|
| 1 | H | 5 | 30 |
| 2 | R | −45 | 50 |
| 3 | H | −45 | 60 |
| 4 | R | −20 | 25 |
| 5 | H | −20 | 240 |
| 6 | R | −45 | 25 |
| 7 | H | −45 | 60 |

Freeze, Condenser and Evacuate:

| | | |
|---|---|---|
| Freeze Temperature: | −45 | deg C. Shelf or Product Ave |
| Extra Freeze Time: | 1 | minutes |
| Vacuum Start Permit: | −40 | Avg Cond deg C. |
| Heat Start Permit: | 300 | mTorr |

Primary Drying

| Step | Rate/Hold | deg C. | Minutes | mTorr |
|---|---|---|---|---|
| 1 | H | −45 | 30 | 150 |
| 2 | R | −28 | 80 | 150 |
| 3 | H | −28 | 900 | 150 |
| 4 | R | −15 | 20 | 150 |
| 5 | H | −15 | 180 | 150 |
| 6 | R | −5 | 20 | 150 |
| 7 | H | −5 | 180 | 150 |
| 8 | R | 27 | 100 | 150 |

Secondary Drying

| Step | | | | |
|---|---|---|---|---|
| 1 | H | 27 | 540 | 100 |

What is claimed is:

1. A liquid composition comprising:

a botulinum toxin, a non-reducing disaccharide or a non-reducing trisaccharide present in an amount of 10% to 40% (w/v);

a non-ionic surfactant present in an amount of 0.005% to 0.5% (w/v); and a physiologically compatible buffer; wherein the amount of the non-reducing disaccharide or the non-reducing trisaccharide and the amount of the non-ionic surfactant provide for an amorphous, noncrystalline solid composition upon drying of the liquid composition in a manner that precludes crystal formation.

2. The liquid composition according to claim 1, further comprising:

a positively charged backbone selected from (a) a positively charged peptide with an amino acid sequence selected from RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), or YGRKKRRQRRR-G-$(K)_{15}$-G-YGRKKRRQRRR (SEQ ID NO: 3); or (b) a positively charged polypeptide or a nonpeptidyl polymer having covalently attached thereto at least one positively charged efficiency group having an amino acid sequence selected from -$(gly)_{n1}$-$(arg)_{n2}$ (SEQ ID NO: 4), wherein the subscript n1 is an integer of from 0 to 20 and the subscript n2 is independently an odd integer of from 5 to 25; $(gly)_p$-RGRDDRRQRRR-$(gly)_q$ (SEQ ID NO 5); $(gly)_p$-YGRKKRRQRRR-$(gly)_q$(SEQ ID NO 6); (gly)p-RKKRRQRRR-$(gly)_q$, (SEQ ID NO 7); wherein the subscripts p and q are each independently an integer of from 0 to 20.

3. The liquid composition according to claim 2, wherein the positively charged backbone is a positively charged polypeptide.

4. The liquid composition according to claim 3, wherein the positively charged polypeptide is polylysine.

5. The liquid composition according to claim 2, wherein the positively charged backbone is a positively charged nonpeptidyl polymer.

6. The liquid composition according to claim 5, wherein the positively charged nonpeptidyl polymer is a polyalkyleneimine.

7. The liquid composition according to claim 6, wherein the positively charged polyalkyleneimine is polyethyleneimine or polypropyleneimine.

8. The liquid composition according to claim 4, wherein the non-reducing disaccharide or tri-saccharide used to prepare the composition is selected from the group consisting of trehalose dihydrate, anhydrous trehalose, sucrose, raffinose and combinations thereof.

9. The liquid composition according to claim 8, wherein the non-reducing disaccharide used to prepare the composition is selected from sucrose, trehalose dihydrate or anhydrous trehalose.

10. The liquid composition according to claim 8, wherein the non-ionic surfactant used to prepare the composition is selected from the group consisting of polysorbates, sorbitan esters, octylphenol ethylene oxide (TRITON™ X-100), nonylphenol ethoxylate (NP-40), poloxamers and combinations thereof.

11. The liquid composition according to claim 9, wherein the non-ionic surfactant used to prepare the composition is selected from the group consisting of polysorbate 20, polysorbate 40, polysorbate 60, polysorbate 80, sorbitan monolaurate (SPAN® 20), sorbitan monostearate (SPAN® 60), sorbitan tristearate (SPAN® 65), and sorbitan monooleate (SPAN® 80).

12. The liquid composition according to claim 11, wherein the physiologically compatible buffer is selected from the group consisting of citric acid, acetic acid, succinic acid, tartaric acid, maleic acid, histidine, citrate/acetate, citrate/ histidine, citrate/tartrate, maleate/histidine, succinate/histidine, or salts thereof, and phosphate buffer.

13. The liquid composition according to claim 12, wherein the positively charged backbone is the peptide with an amino acid sequence selected from RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), or YGRKKRRQRRR-G-$(K)_{15}$-G-YGRKKRRQRRR (SEQ ID NO: 3).

14. The liquid composition according to claim 12, wherein the positively charged backbone is polylysine having attached thereto at least one positively charged efficiency group selected from amino acid sequence (gly)p-RKKRRQRRR-$(gly)_q$ (SEQ ID NO: 5); $(gly)_p$-RGRDDRRQRRR-$(gly)_q$ (SEQ ID NO: 6); or $(gly)_p$-YGRKKRRQRRR-$(gly)_q$ (SEQ ID NO: 7); wherein the subscripts p and q are each independently an integer of from 0 to 20.

15. The liquid composition according to claim 2, wherein the subscript n1 is an integer of from 0 to 8; and the subscript n2 is independently an odd integer of from 7 to 17; and wherein the subscripts p and q are each independently an integer of from 0 to 8.

16. The liquid composition according to claim 15, wherein the subscript n1 is an integer of from 2 to 5; and the subscript n2 is independently an odd integer of from 7 to 13; and wherein the subscripts p and q are each independently an integer of from 2 to 5.

17. The liquid composition according to claim 14, wherein the subscripts p and q are each independently an integer of from 0 to 8.

18. The liquid composition according to claim 14, wherein the subscripts p and q are each independently an integer of from 2 to 5.

19. The liquid composition according to claim 13, wherein the positively charged backbone is the peptide with the amino acid sequence RKKRRQRRR-G-$(K)_{15}$-G-RKKRRQRRR (SEQ ID NO: 1).

20. The liquid composition according to claim 13, wherein the positively charged backbone is the peptide with the amino acid sequence RGRDDRRQRRR-G-$(K)_{15}$-G-RGRDDRRQRRR (SEQ ID NO: 2).

21. The liquid composition according to claim 13, wherein the positively charged backbone is the peptide with the amino acid sequence YGRKKRRQRRR-G-$(K)_{15}$-G-YGRKKRRQRRR (SEQ ID NO: 3).

22. The liquid composition according to claim 4, wherein the botulinum toxin is selected from botulinum toxin of serotype A, B, C, D, E, F, or G.

23. The liquid composition according to claim 13, wherein the botulinum toxin is botulinum toxin of serotype A.

24. The liquid composition according to claim 13, wherein the botulinum toxin is a 150 kD botulinum toxin.

25. The liquid composition according to claim 13, wherein the botulinum toxin of serotype A is a 150 kD botulinum toxin.

26. The liquid composition according to claim 23, further comprising a gelling agent, a viscosity-modifying agent, or a combination thereof.

27. The liquid composition according to claim 26, wherein the gelling agent is a cellulose-based gelling agent and/or the viscosity-modifying agent is selected from one or more of polyethylene glycol, a poloxamer, a polyacrylic acid, a polyamide, or a vegetable gum.

28. The liquid composition according to claim 27, wherein the viscosity-modifying agent is a poloxamer.

29. The liquid composition according to claim 28, wherein the viscosity-modifying agent is a poloxamer selected from poloxamer 181, poloxamer 188, or poloxamer 407.

30. The liquid composition according to claim 25, wherein the non-reducing disaccharide or the non-reducing trisaccharide is present in an amount of from 10% to 25% (w/v).

31. The liquid composition according to claim 30, wherein the non-reducing disaccharide or the non-reducing trisaccharide is present in an amount of from 15% to 20% (w/v).

32. The liquid composition according to claim 31, wherein the non-reducing disaccharide or the non-reducing trisaccharide is present in an amount of 18% (w/v).

33. The liquid composition according to claim 30, wherein the non-ionic surfactant is present in an amount of from 0.01% to 0.2% (w/v).

34. The liquid composition according to claim 33, wherein the non-ionic surfactant is present in an amount of from 0.02% to 0.1%.

35. The liquid composition according to claim 34, wherein the non-ionic surfactant is present in an amount of from 0.05% to 0.08%.

36. The liquid composition according to claim 32, wherein the non-ionic surfactant is present in an amount of 0.05% (w/v).

37. The liquid composition according to claim 33, wherein the pH of the composition is from 4.5 to 6.5.

38. The liquid composition according to claim 25, wherein the composition does not contain animal-derived proteinaceous excipients.

39. The liquid composition according to claim 38, wherein the composition does not contain albumin.

40. The liquid composition according to claim 39, comprising a formulation bulk drug product.

41. The liquid composition according to claim 25, wherein the botulinum toxin is present in an amount ranging from 400 U to 3,000 U.

42. The liquid composition according to claim 41, wherein the botulinum toxin is present in an amount of 1,000 U to 2,500 U.

43. The liquid composition according to claim 23, wherein the botulinum toxin is present in an amount of 10 U to 400 U.

44. The liquid composition according to claim 23, wherein the botulinum toxin is present in an amount of 400 U to 800 U.

45. The liquid composition according to claim 23, wherein the botulinum toxin is present in an amount of 10 U to 150 U.

46. The liquid composition according to claim 23, wherein the botulinum toxin is present in an amount of about 200 U to about 400 U.

47. The liquid composition according to claim 23, wherein the botulinum toxin is present in an amount of about 200 U to about 300 U.

48. The liquid composition according to claim 23, wherein the botulinum toxin is present in an amount of about 200 U to about 275 U.

49. The liquid composition according to claim 25, wherein the botulinum toxin is present in an amount suitable for topical administration.

50. The liquid composition according to claim 49, wherein the botulinum toxin is present in a therapeutically or cosmeceutically effective amount ranging from 1,000 U to 50,000 U suitable for topical administration.

51. The liquid composition according to claim 50, wherein the botulinum toxin is present in a therapeutically or cosmeceutically effective amount ranging from 2,000 U to 35,000 U suitable for topical administration.

52. The liquid composition according to claim 51, wherein the botulinum toxin is present in a therapeutically or cosmeceutically effective amount ranging from 4,000 U to 25,000 U suitable for topical administration.

53. The liquid composition according to claim 52, wherein the botulinum toxin is present in a therapeutically or cosmeceutically effective amount ranging from 4,000 U to 8,000 U suitable for topical administration.

54. The liquid composition according to claim 52, wherein the botulinum toxin is present in a therapeutically or cosmeceutically effective amount ranging from 9,000 U to 19,000 U suitable for topical administration.

55. The liquid composition according to claim 2, wherein the liquid composition is dried by lyophilization to produce a solid composition.

56. The solid composition according to 55, wherein the solid composition is a powder.

57. The solid composition according to 55, wherein solid composition is a lyophilized cake.

58. An amorphous, noncrystalline solid composition produced by lyophilization of a liquid composition, said liquid composition comprising:

a botulinum toxin;

a non-reducing disaccharide or a non-reducing trisaccharide present in an amount of 10% to 40% (by weight);

a non-ionic surfactant present in an amount of 0.005% to 0.5% (by weight); and a physiologically compatible buffer.

59. The solid composition according to claim 58, further comprising:

a positively charged backbone selected from (a) a positively charged peptide with an amino acid sequence selected from RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), or YGRKKRRQRRR-G-$(K)_{15}$-G-YGRKKRRQRRR (SEQ ID NO: 3); or (b) a positively charged polypeptide or a nonpeptidyl polymer having covalently attached thereto at least one positively charged efficiency group having an amino acid sequence selected from -$(gly)_{n1}$-$(arg)_{n2}$ (SEQ ID NO: 4), wherein the subscript n1 is an integer of from 0 to 20 and the subscript n2 is independently an odd integer of from 5 to 25; $(gly)_p$-RGRDDRRQRRR-$(gly)_q$ (SEQ ID NO 5); $(gly)_p$-YGRKKRRQRRR-$(gly)_q$ (SEQ ID NO 6); (gly)p-RKKRRQRRR-$(gly)_q$, (SEQ ID NO 7); wherein the subscripts p and q are each independently an integer of from 0 to 20.

60. The solid composition according to claim 59, wherein the positively charged backbone is a positively charged polypeptide.

61. The solid composition according to claim 60, wherein the positively charged polypeptide is polylysine.

62. The solid composition according to claim 59, wherein the positively charged backbone is a positively charged nonpeptidyl polymer.

63. The solid composition according to claim 62, wherein the positively charged nonpeptidyl polymer is a polyalkyleneimine.

64. The solid composition according to claim 63, wherein the positively charged polyalkyleneimine is polyethyleneimine or polypropyleneimine.

65. The solid composition according to claim 61, wherein the non-reducing disaccharide or tri-saccharide used to prepare the liquid composition is selected from the group consisting of trehalose dihydrate, anhydrous trehalose, sucrose, raffinose and combinations thereof.

66. The solid composition according to claim 65, wherein the non-reducing disaccharide used to prepare the liquid composition is selected from sucrose, trehalose dihydrate or anhydrous trehalose.

67. The solid composition according to claim 65, wherein the non-ionic surfactant used to prepare the liquid composition is selected from the group consisting of polysorbates, sorbitan esters, octylphenol ethylene oxide (TRITON™ X-100), nonylphenol ethoxylate (NP-40), poloxamers and combinations thereof.

68. The solid composition according to claim 66, wherein the non-ionic surfactant used to prepare the liquid composition is selected from the group consisting of polysorbate 20, polysorbate 40, polysorbate 60, polysorbate 80, sorbitan monolaurate (SPAN® 20), sorbitan monostearate (SPAN® 60), sorbitan tristearate (SPAN® 65), and sorbitan monooleate (SPAN® 80).

69. The solid composition according to claim 68, wherein the physiologically compatible buffer used to prepare the liquid compositions is selected from the group consisting of citric acid, acetic acid, succinic acid, tartaric acid, maleic acid, histidine, citrate/acetate, citrate/histidine, citrate/tartrate, maleate/histidine, succinate/histidine, or salts thereof, and phosphate buffer.

70. The solid composition according to claim 69, wherein the positively charged backbone is the peptide with an amino acid sequence selected from RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), or YGRKKRRQRRR-G-$(K)_{15}$-G-YGRKKRRQRRR (SEQ ID NO: 3).

71. The solid composition according to claim 69, wherein the positively charged backbone is polylysine having attached thereto at least one positively charged efficiency group selected from amino acid sequence (gly)p-RKKRRQRRR-$(gly)_q$ (SEQ ID NO: 5); $(gly)_p$-RGRDDRRQRRR-$(gly)_q$ (SEQ ID NO: 6); or $(gly)_p$-YGRKKRRQRRR-$(gly)_q$ (SEQ ID NO: 7); wherein the subscripts p and q are each independently an integer of from 0 to 20.

72. The solid composition according to claim 59, wherein the subscript n1 is an integer of from 0 to 8; and the subscript n2 is independently an odd integer of from 7 to 17; and wherein the subscripts p and q are each independently an integer of from 0 to 8.

73. The solid composition according to claim 72, wherein the subscript n1 is an integer of from 2 to 5; and the subscript n2 is independently an odd integer of from 7 to 13; and wherein the subscripts p and q are each independently an integer of from 2 to 5.

74. The solid composition according to claim 71, wherein the subscripts p and q are each independently an integer of from 0 to 8.

75. The solid composition according to claim 71, wherein the subscripts p and q are each independently an integer of from 2 to 5.

76. The solid composition according to claim 70, wherein the positively charged backbone is the peptide with the amino acid sequence RKKRRQRRR-G-$(K)_{15}$-G-RKKRRQRRR (SEQ ID NO: 1).

77. The solid composition according to claim 70, wherein the positively charged backbone is the peptide with the amino acid sequence RGRDDRRQRRR-G-$(K)_{15}$-G-RGRDDRRQRRR (SEQ ID NO: 2).

78. The solid composition according to claim 70, wherein the positively charged backbone is the peptide with the amino acid sequence YGRKKRRQRRR-G-$(K)_{15}$-G-YGRKKRRQRRR (SEQ ID NO: 3).

79. The solid composition according to claim 61, wherein the botulinum toxin is selected from botulinum toxin of serotype A, B, C, D, E, F, or G.

80. The solid composition according to claim 70, wherein the botulinum toxin is botulinum toxin of serotype A.

81. The solid composition according to claim 70, wherein the botulinum toxin is a 150 kD botulinum toxin.

82. The solid composition according to claim 80, wherein the botulinum toxin of serotype A is a 150 kD botulinum toxin.

83. The solid composition according to claim 80, further comprising a gelling agent, a viscosity-modifying agent, or a combination thereof.

84. The solid composition according to claim 83, wherein the gelling agent is a cellulose-based gelling agent and/or the viscosity-modifying agent is selected from one or more of polyethylene glycol, a poloxamer, a polyacrylic acid, a polyamide, or a vegetable gum.

85. The solid composition according to claim 84, wherein the viscosity-modifying agent is a poloxamer.

86. The solid composition according to claim 85, wherein the viscosity-modifying agent is a poloxamer selected from poloxamer 181, poloxamer 188, or poloxamer 407.

87. The solid composition according to claim 82, wherein the solid composition is produced by lyophilization of the liquid composition comprising a non-reducing disaccharide or a non-reducing trisaccharide present in an amount of from 10% to 25% (w/v).

88. The solid composition according to claim 87, wherein the solid composition is produced by lyophilization of the liquid composition comprising a non-reducing disaccharide or a non-reducing trisaccharide present in an amount of from 15% to 20% (w/v).

89. The solid composition according to claim 88, wherein the solid composition is produced by lyophilization of the liquid composition comprising a non-reducing disaccharide or a non-reducing trisaccharide in an amount of 18% (w/v).

90. The solid composition according to claim 87, wherein the solid composition is produced by lyophilization of the liquid composition comprising a non-ionic surfactant in an amount of from 0.01% to 0.2% (w/v).

91. The solid composition according to claim 90, wherein the solid composition is produced by lyophilization of the liquid composition comprising a non-ionic surfactant in an amount of from 0.02% to 0.1%.

92. The solid composition according to claim 91, wherein the solid composition is produced by lyophilization of the liquid composition comprising a non-ionic surfactant in an amount of from 0.05% to 0.08%.

93. The solid composition according to claim 89, wherein the solid composition is produced by lyophilization of the liquid composition comprising a non-ionic surfactant in an amount of from 0.05% (w/v).

94. The solid composition according to claim 90, wherein the pH of the composition is from 4.5 to 6.5.

95. The solid composition according to claim 82, wherein the composition does not contain animal-derived proteinaceous excipients.

96. The solid composition according to claim 95, wherein the composition does not contain albumin.

97. The solid composition according to claim 96, comprising a formulation bulk drug product.

98. The solid composition according to claim 82, wherein the botulinum toxin is present in an amount of 400 U to 3,000 U.

99. The solid composition according to claim 98, wherein the botulinum toxin is present in an amount of 1,000 U to 2,500 U.

100. The solid composition according to claim 80, wherein the botulinum toxin is present in an amount of 10 U to 400 U.

101. The solid composition according to claim 80, wherein the botulinum toxin is present in an amount of 400 U to 800 U.

102. The solid composition according to claim 80, wherein the botulinum toxin is present in an amount of 10 U to 150 U.

103. The solid composition according to claim 80, wherein the botulinum toxin is present in an amount of about 200 U to about 400 U.

104. The solid composition according to claim 80, wherein the botulinum toxin is present in an amount of about 200 U to about 300 U.

105. The solid composition according to claim 80, wherein the botulinum toxin is present in an amount of about 200 U to about 275 U.

106. The solid composition according to claim 82, wherein the botulinum toxin is present in an amount suitable for topical administration.

107. The solid composition according to claim 106, wherein the botulinum toxin is present in a therapeutically or cosmeceutically effective amount ranging from 1,000 U to 50,000 U suitable for topical administration.

108. The solid composition according to claim 107, wherein the botulinum toxin is present in a therapeutically or cosmeceutically effective amount ranging from 2,000 U to 35,000 U suitable for topical administration.

109. The solid composition according to claim 108, wherein the botulinum toxin is present in a therapeutically or cosmeceutically effective amount ranging from 4,000 U to 25,000 U suitable for topical administration.

110. The solid composition according to claim 109, wherein the botulinum toxin is present in a therapeutically effective amount ranging from 4,000 U to 8,000 U suitable for topical administration.

111. The solid composition according to claim 109, wherein the botulinum toxin is present in a therapeutically or cosmeceutically effective amount ranging from 9,000 U to 19,000 U suitable for topical administration.

112. The solid composition according to claim 59, wherein the composition is a powder.

113. The solid composition according to claim 59, wherein the composition is an amorphous cake.

114. A kit comprising the solid composition according to claim 57, and a syringe.

115. A kit comprising the solid composition according to claim 113, and a syringe.

116. The kit according to claim 114, wherein the solid composition does not contain animal-derived proteinaceous excipients.

117. The kit according to claim 115, wherein the solid composition does not contain animal-derived proteinaceous excipients.

118. The kit according to claim 116, wherein the solid composition does not contain albumin.

119. The kit according to claim 117, wherein the solid composition does not contain albumin.

120. An amorphous noncrystalline solid composition produced by lyophilization of a liquid composition, said liquid composition comprising a botulinum toxin A protein of 150 kD; a non-reducing disaccharide or a non-reducing trisaccharide in an amount of from 10% to 20%, by weight; a non-ionic surfactant in an amount of selected from 0.01% to 0.15% by weight; a positively charged peptide having an amino acid sequence selected from the group consisting of RKKRRQRRR-G-$(K)_{15}$-G-RKKRRQRRR (SEQ ID NO: 1), RGRDDRRQRRR-G-$(K)_{15}$-G-RGRDDRRQRRR (SEQ ID NO: 2), and YGRKKRRQRRR-G-$(K)_{15}$-G-YGRKKRRQRRR (SEQ ID NO: 3); and a physiologically compatible buffer.

121. The solid composition according to claim 120, wherein the non-reducing disaccharide or the non-reducing trisaccharide used to prepare the liquid composition is selected from the group consisting of trehalose dihydrate, anhydrous trehalose, sucrose, raffinose and combinations thereof; and wherein the non-ionic surfactant used to prepare the liquid composition is selected from the group consisting of polysorbates, sorbitan esters, octylphenol ethylene oxide (TRITON™ X-100), nonylphenol ethoxylate (NP-40), poloxamers and combinations thereof.

122. The solid composition according to claim 121, wherein the non-reducing disaccharide or the non-reducing trisaccharide used to prepare the liquid composition is sucrose, trehalose dihydrate or anhydrous trehalose; and wherein the non-ionic surfactant used to prepared the liquid composition is a polysorbate.

123. The solid composition according to claim 122, wherein the physiologically compatible buffer used to prepare the liquid composition is selected from the group consisting of citric acid, acetic acid, succinic acid, tartaric acid, maleic acid, histidine, citrate/acetate, citrate/histidine, citrate/tartrate, maleate/histidine, succinate/histidine, or salts thereof, and phosphate buffer.

124. The solid composition according to claim 123, wherein the positively charged peptide has the amino acid sequence RKKRRQRRR-G-$(K)_{15}$-G-RKKRRQRRR (SEQ ID NO: 1).

125. The solid composition according to claim 123, wherein the positively charged peptide has the amino acid sequence RGRDDRRQRRR-G-$(K)_{15}$-G-RGRDDRRQRRR (SEQ ID NO: 2).

126. The solid composition according to claim 123, wherein the positively charged peptide has the amino acid sequence YGRKKRRQRRR-G-$(K)_{15}$-G-YGRKKRRQRRR (SEQ ID NO: 3).

127. The solid composition according to claim 123, further comprising a gelling agent, a viscosity-modifying agent, or a combination thereof; wherein the gelling agent is optionally a cellulose-based gelling agent and/or the viscosity-modifying agent is optionally selected from one or more of polyethylene glycol, a poloxamer, a polyacrylic acid, a polyamide, or a vegetable gum.

128. The solid composition according to claim 127, wherein the composition is for topical administration and the botulinum toxin is present in a therapeutically or cosmeceutically effective amount ranging from 2,000 U to 35,000 U suitable for topical administration.

129. The solid composition according to claim 124, wherein the physiologically compatible buffer used to prepare the liquid composition is histidine or a salt thereof.

130. The solid composition according to claim 129, wherein the non-reducing disaccharide or tri-saccharide used to prepare the composition is sucrose.

131. The solid composition according to claim 130, wherein the non-ionic surfactant used to prepared the liquid composition is polysorbate 20.

132. The solid composition according to claim 131, wherein the non-reducing disaccharide or the non-reducing trisaccharide used to prepare the liquid composition is present in an amount of 18% (w/v); and wherein the non-ionic surfactant used to prepared the liquid composition is present in an amount of 0.05% (w/v).

133. The solid composition according to claim 132, wherein the pH of the composition is from 4.5 to 6.5.

134. The solid composition according to claim 132, wherein the pH of the composition is 6.5.

135. The liquid composition according to claim 36, wherein the non-ionic surfactant used to prepare the liquid composition is polysorbate 20.

136. The liquid composition according to claim 135, wherein the non-reducing disaccharide or tri-saccharide used to prepare the liquid composition is sucrose.

137. The liquid composition according to claim 136, wherein the positively charged backbone is the peptide with the amino acid sequence RKKRRQRRR-G-$(K)_{15}$-G-RKKRRQRRR (SEQ ID NO: 1).

138. The liquid composition according to claim 137, wherein the physiologically compatible buffer used to prepare the liquid composition is histidine or a salt thereof.

139. The liquid composition according to claim 138, wherein the pH of the composition is from 4.5 to 6.5.

140. The liquid composition according to claim 139, wherein the pH of the composition is 6.5.

141. The solid composition according to claim 93, wherein the non-ionic surfactant used to prepared the liquid composition is polysorbate 20.

142. The solid composition according to claim 141, wherein the non-reducing disaccharide or tri-saccharide used to prepare the composition is sucrose.

143. The solid composition according to claim 142, wherein the positively charged backbone is the peptide with the amino acid sequence RKKRRQRRR-G-$(K)_{15}$-G-RKKRRQRRR (SEQ ID NO: 1).

144. The solid composition according to claim 143, wherein the physiologically compatible buffer used to prepare the liquid composition is histidine or a salt thereof.

145. The solid composition according to claim 144, wherein the pH of the composition is from 4.5 to 6.5.

146. The solid composition according to claim 145, wherein the pH of the composition is 6.5.

* * * * *

UNITED STATES PATENT AND TRADEMARK OFFICE

CERTIFICATE OF CORRECTION

PATENT NO. : 9,340,587 B2
APPLICATION NO. : 12/824118
DATED : May 17, 2016
INVENTOR(S) : Stewart A. Thompson et al.

It is certified that error appears in the above-identified patent and that said Letters Patent is hereby corrected as shown below:

In the Claims

Claim 14, Column 25, Lines 13-14, "$(gly)_p$ -RKKRRQRRR-$(gly)_q$ (SEQ ID NO: 5)" should read --$(gly)_p$-RKKRRQRRR-$(gly)_q$ (SEQ ID NO: 7)--.

Claim 14, Column 25, Lines 14-15, "$(gly)_p$-RGRDDRRQRRR-$(gly)_q$ (SEQ ID NO: 6)" should read --$(gly)_p$-RGRDDRRQRRR-$(gly)_q$ (SEQ ID NO: 5)--.

Claim 14, Column 25, Lines 15-16, "$(gly)_p$-YGRKKRRQRRR-$(gly)_q$ (SEQ ID NO: 7)" should read --$(gly)_p$- YGRKKRRQRRR -$(gly)_q$ (SEQ ID NO: 6)--.

Claim 71, Column 28, Lines 35-36, "$(gly)_p$ -RKKRRQRRR-$(gly)_q$ (SEQ ID NO: 5)" should read --$(gly)_p$ -RKKRRQRRR-$(gly)_q$ (SEQ ID NO: 7)--.

Claim 71, Column 28, Lines 36-37, "$(gly)_p$ -RGRDDRRQRRR-$(gly)_q$ (SEQ ID NO: 6)" should read --$(gly)_p$-RGRDDRRQRRR-$(gly)_q$ (SEQ ID NO: 5)--.

Claim 71, Column 28, Lines 37-38, "$(gly)_p$ -YGRKKRRQRRR-$(gly)_q$ (SEQ ID NO: 7)" should read --$(gly)_p$- YGRKKRRQRRR -$(gly)_q$ (SEQ ID NO: 6)--.

Signed and Sealed this
Twenty-second Day of November, 2022

Katherine Kelly Vidal

Katherine Kelly Vidal
*Director of the United States Patent and Trademark Office*